(12) United States Patent
Endo et al.

(10) Patent No.: US 9,738,667 B2
(45) Date of Patent: Aug. 22, 2017

(54) PHOSPHORUS-CONTAINING COMPOUND AND CURING EPOXY RESIN COMPOSITION CONTAINING SAME

(71) Applicant: ADEKA CORPORATION, Tokyo (JP)

(72) Inventors: Takeshi Endo, Fukuoka (JP); Kozo Matsumoto, Fukuoka (JP); Ken-ichi Tamaso, Saitama (JP); Ryo Ogawa, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/915,766

(22) PCT Filed: Nov. 10, 2014

(86) PCT No.: PCT/JP2014/073994
§ 371 (c)(1),
(2) Date: Mar. 1, 2016

(87) PCT Pub. No.: WO2015/049965
PCT Pub. Date: Apr. 9, 2015

(65) Prior Publication Data
US 2016/0200747 A1    Jul. 14, 2016

(30) Foreign Application Priority Data
Oct. 1, 2013 (JP) .................... 2013-206637

(51) Int. Cl.
*C07F 9/24* (2006.01)
*C07F 9/22* (2006.01)
*C08G 59/40* (2006.01)
*C08G 59/44* (2006.01)
*C08G 59/14* (2006.01)

(52) U.S. Cl.
CPC .......... *C07F 9/242* (2013.01); *C07F 9/224* (2013.01); *C07F 9/2404* (2013.01); *C07F 9/2458* (2013.01); *C08G 59/1488* (2013.01); *C08G 59/4071* (2013.01); *C08G 59/446* (2013.01)

(58) Field of Classification Search
CPC .................. C07F 9/242; C07F 9/224
See application file for complete search history.

(56) References Cited

U.S. PATENT DOCUMENTS

| | | | |
|---|---|---|---|
| 3,475,536 A * | 10/1969 | Landram | C07F 9/062 514/138 |
| 3,502,690 A * | 3/1970 | Schroder | C07F 7/22 544/139 |
| 3,531,550 A | 9/1970 | Herber et al. | |
| 3,645,971 A | 2/1972 | Hindersinn | |
| 3,764,374 A | 10/1973 | Barton et al. | |
| 4,086,302 A | 4/1978 | Morgan et al. | |

FOREIGN PATENT DOCUMENTS

| | | |
|---|---|---|
| CN | 102617637 | 8/2012 |
| DE | 2338506 | 2/1974 |
| GB | 1333276 | 10/1973 |
| GB | 1435569 | 5/1976 |
| GB | 1494774 | 12/1977 |
| JP | S4975821 | 7/1974 |
| JP | 50-82150 | 7/1975 |
| JP | 08-337709 | 12/1996 |
| JP | 10-195178 | 7/1998 |
| JP | 10-265487 | 10/1998 |

OTHER PUBLICATIONS

Wade et al (1970): STN International HCAPLUS database, (Columbus, Ohio), Accession No. 1970:24625.*
Hamed et al (2007): STN International HCAPLUS database, (Columbus, Ohio), Accession No. 2007:379592.*
Rittig et al (2008): STN International HCAPLUS database, (Columbus, Ohio), Accession No. 2008:252741.*
International Search Report, PCT/JP2014/073994, Dec. 9, 2014.
Roth, Hermann J. et al., Synthesis of phenyl phosphorodiamidates. I, Archiv der Pharmazie, 1981, 314 (1), 85-91 (Scheme I, II).
Quast, Helmut et al., Three-membered heterocycles. 10. Phosphonohydrazidic esters by alkoxide-induced rearrangement of N-chlorophosphonic diamides, Liebigs Annalen der Chemie, 1981, (5), 943-66 (p. 945).
Skrowaczewska, Zofia et al., Action of hydrogen halides upon the P-N bond in some amide derivatives of phosphoric acid, Roczniki Chemii, 1955, 29, 415-30 (particularly, p. 411).
Buina, N. A. et al., Synthesis and addition reactions of arylphosphorus acid tetraethyldiamides, Izvestiya Akademii Nauk SSSR, Seriya Khimicheskaya, 1967, (7), 1606-8 (particularly, p. 1607).

(Continued)

*Primary Examiner* — Golam M M Shameem
(74) *Attorney, Agent, or Firm* — Young & Thompson

(57) ABSTRACT

Provided is a novel phosphorus-containing compound represented by general formula (I). The compound has reactivity with a glycidyl group and is therefore capable of providing a curing epoxy resin composition that is expected to achieve flame retardation and reduction of dielectric constant.

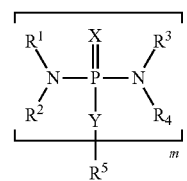

wherein m is a number of 1 to 10; $R^1$, $R^2$, $R^3$, and $R^4$ are each hydrogen, alkyl, or aryl; $R^5$ is alkyl, alkanediyl, alkanetriyl, alkanetetrayl, or an aromatic group; X is oxygen or sulfur; Y is oxygen, sulfur, or =NR'; and R' is hydrogen, alkyl, or aryl.

6 Claims, 17 Drawing Sheets

(56) References Cited

OTHER PUBLICATIONS

Kenji Yamazaki et al., "Directed Ortho Borylation of Phenol Derivatives Catalyzed by a Silica-Supported Iridium Complex", Organic Letters, 2010, vol. 12, No. 18, pp. 3978-3981.

Supplementary European Search Report dated Jan. 30, 2017 in corresponding European Patent Application No. 14850484.8.

Ping-Lin Kuo et al., "Flame-Retarding Materials, 3a. Tailor-Made Thermal Stability Epoxy Curing Agents Containing Difunctional Phosphoric Amide Groups", Macromolecular Chemistry and Physics, vol. 202, No. 11, Jul. 2001, pp. 2175-2180, XP055334584, DE, ISSN: 1022-1352.

E.N. Rasadkina et al., "1,3-Dihydroxynaphthalene in the Synthesis of Phosphorus-containing Macroheterocycles", Russian Journal of General Chemistry, vol. 75, No. 12, Dec. 2005, pp. 1910-1918, XP019300955, ISSN: 1608-3350.

E.N. Rasadkina et al., "Cyclobisphosphorylation of 1,7-Dihydroxynaphthalene with Phosphorous Triamides", Russian Journal of General Chemistry, vol. 74, No. 1, Jan. 2004, pp. 48-57, XP055334544, RU, ISSN: 1070-3632.

E.E. Nifant'ev et al., "Phosphacyclophanes Derived from Hydroquinone and 4,4'-Dihydroxybiphenyl", Russian Journal of General Chemistry, vol. 71, No. 3, Jan. 2001, pp. 366-372, XP055334546, RU, ISSN: 1070-3632.

P.V. Slitikov et al., "Cyclic bis-amidophosphites based on 1,6-dihydroxynaphthalene", Russian Chemical Bulletin, International Edition, vol. 62, No. 9, Sep. 2013, pp. 2023-2031, XP055334520, US, ISSN: 1066-5285.

F. Zetsche et al., "Ester der Mono- and Dianilido-phosphorsaure", Chem. Ber., Jan. 1940, pp. 47-49, XP055334563, retrieved from the internet: URL:http://onlinelibrary.wiley.com/store/10.1002/cber.19400730110/asset/19400730110ftp.pdf?v=1&t=ixu4q9vz&s=df9fdd28d2ace9f776cec1e31be9da22b57529d0 [retrieved on Jan. 12, 2017].

Edward E. Nifantyev et al., "Anthracene Diols in the Synthesis of Phosphacyclophanes", Phosphorus, Sulfur, and Silicon and the Related Elements, vol. 182, No. 6, Apr. 2007, pp. 1413-1424, XP055334528, US, ISSN: 1042-6507.

* cited by examiner

[Fig.1]
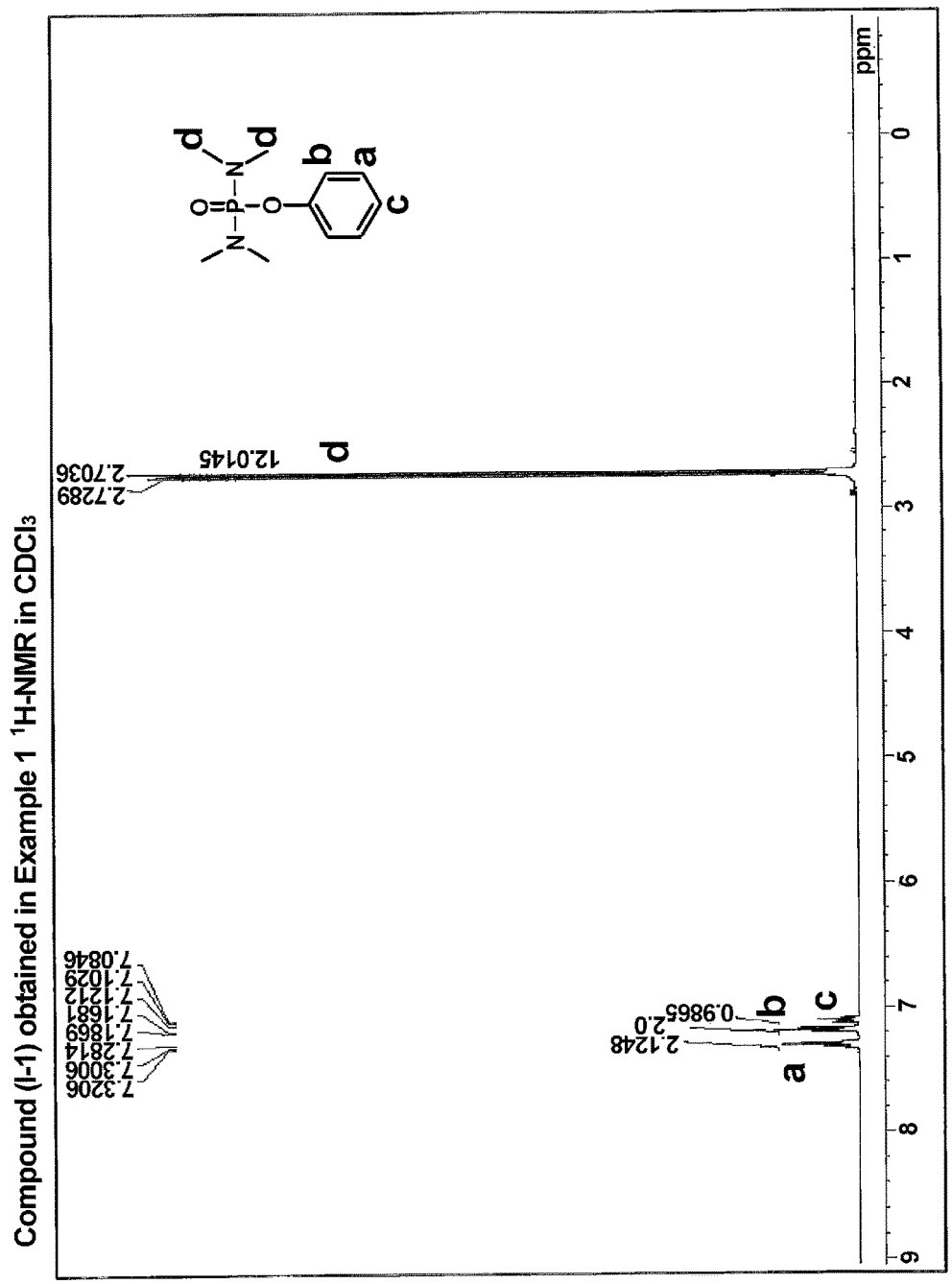

[Fig.2]
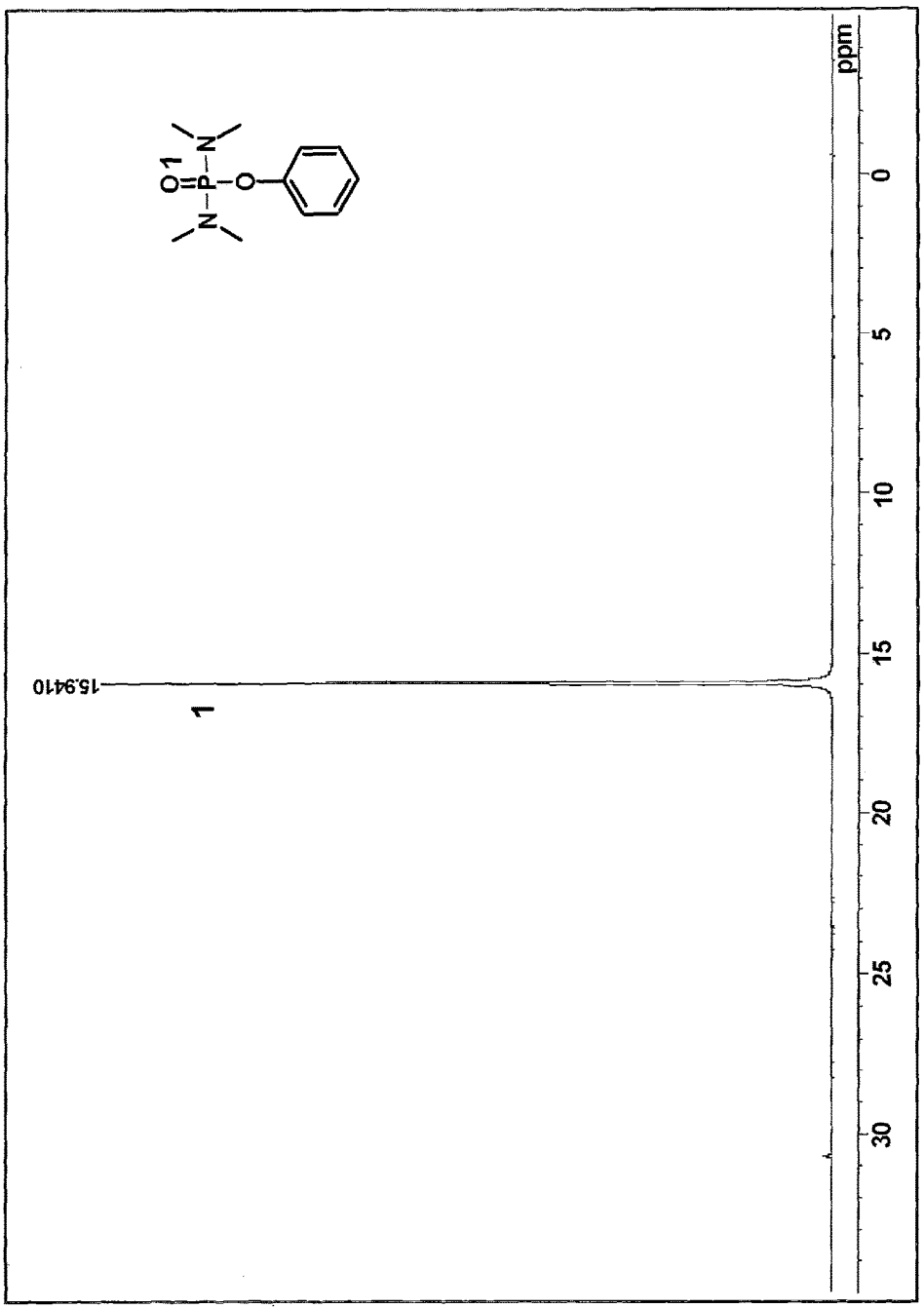

[Fig.3]
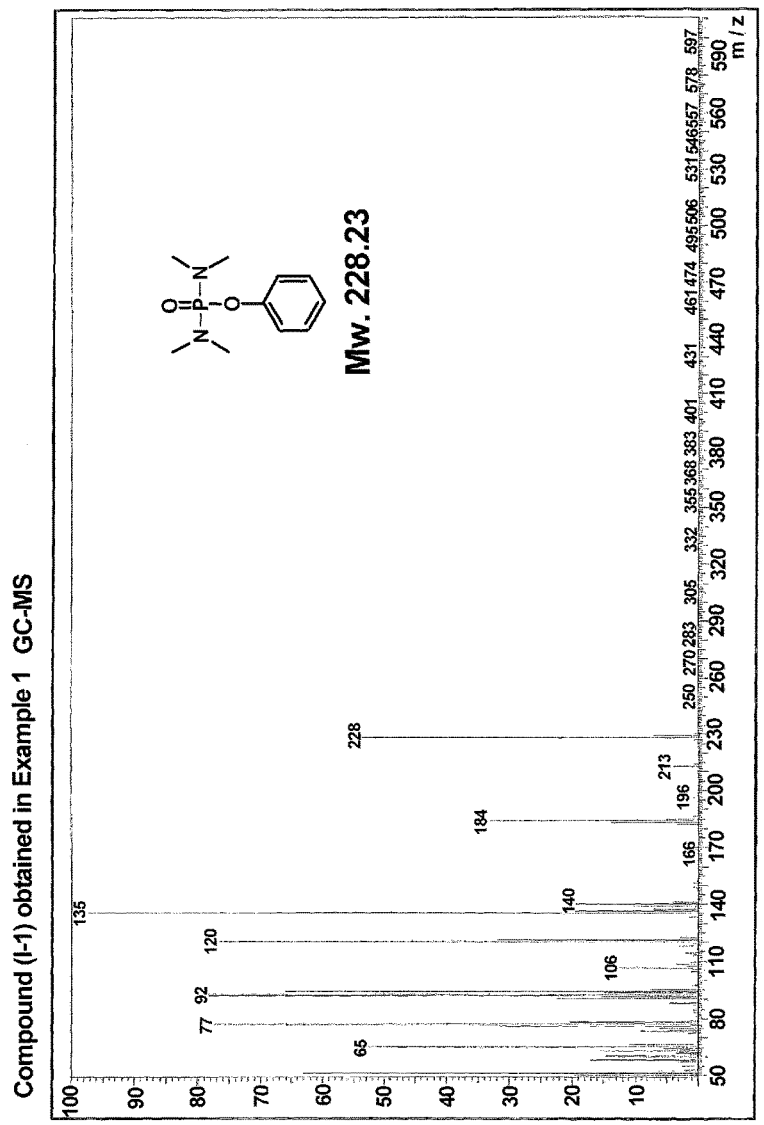

[Fig.4]
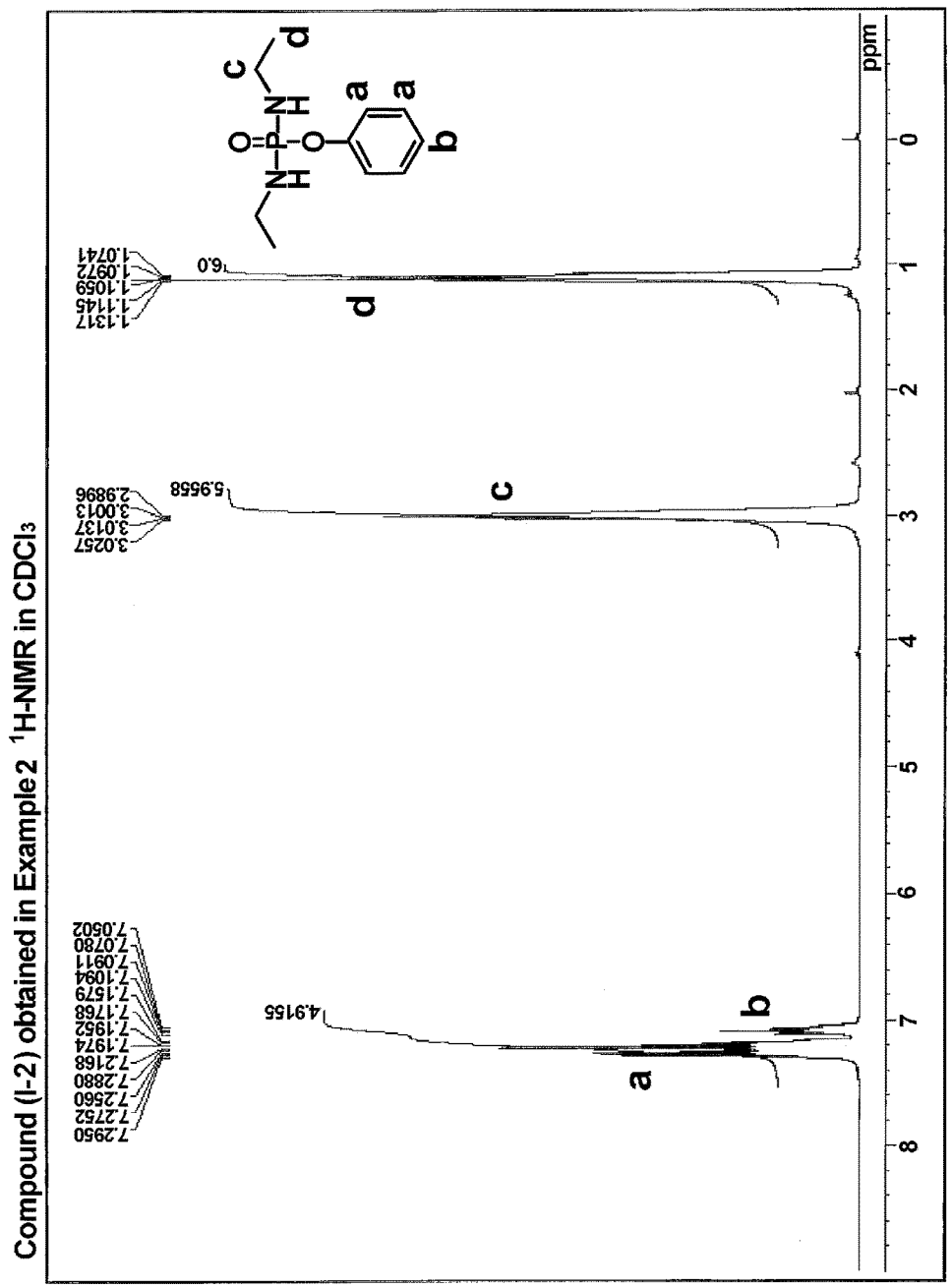

[Fig.5]
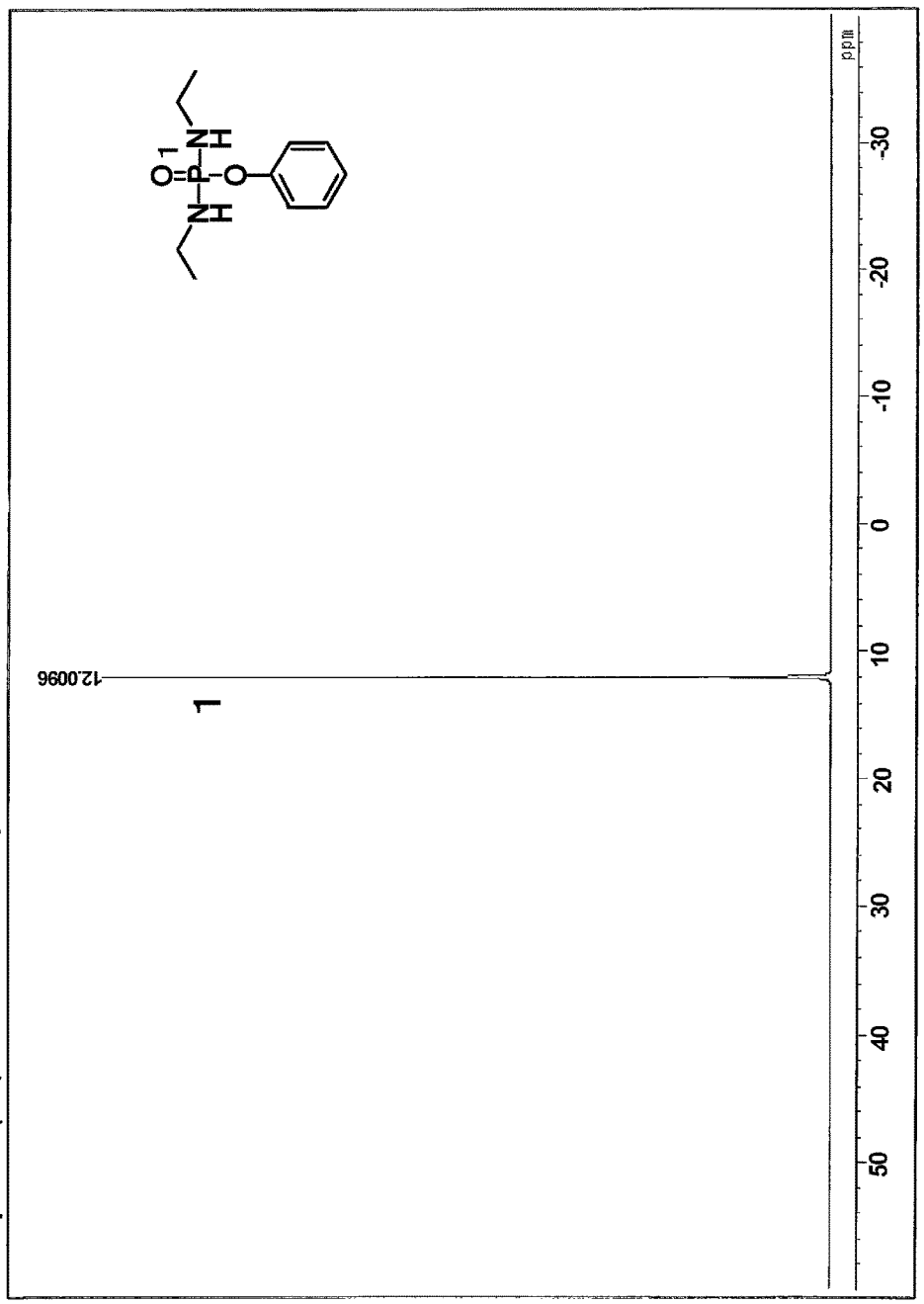

[Fig.6]
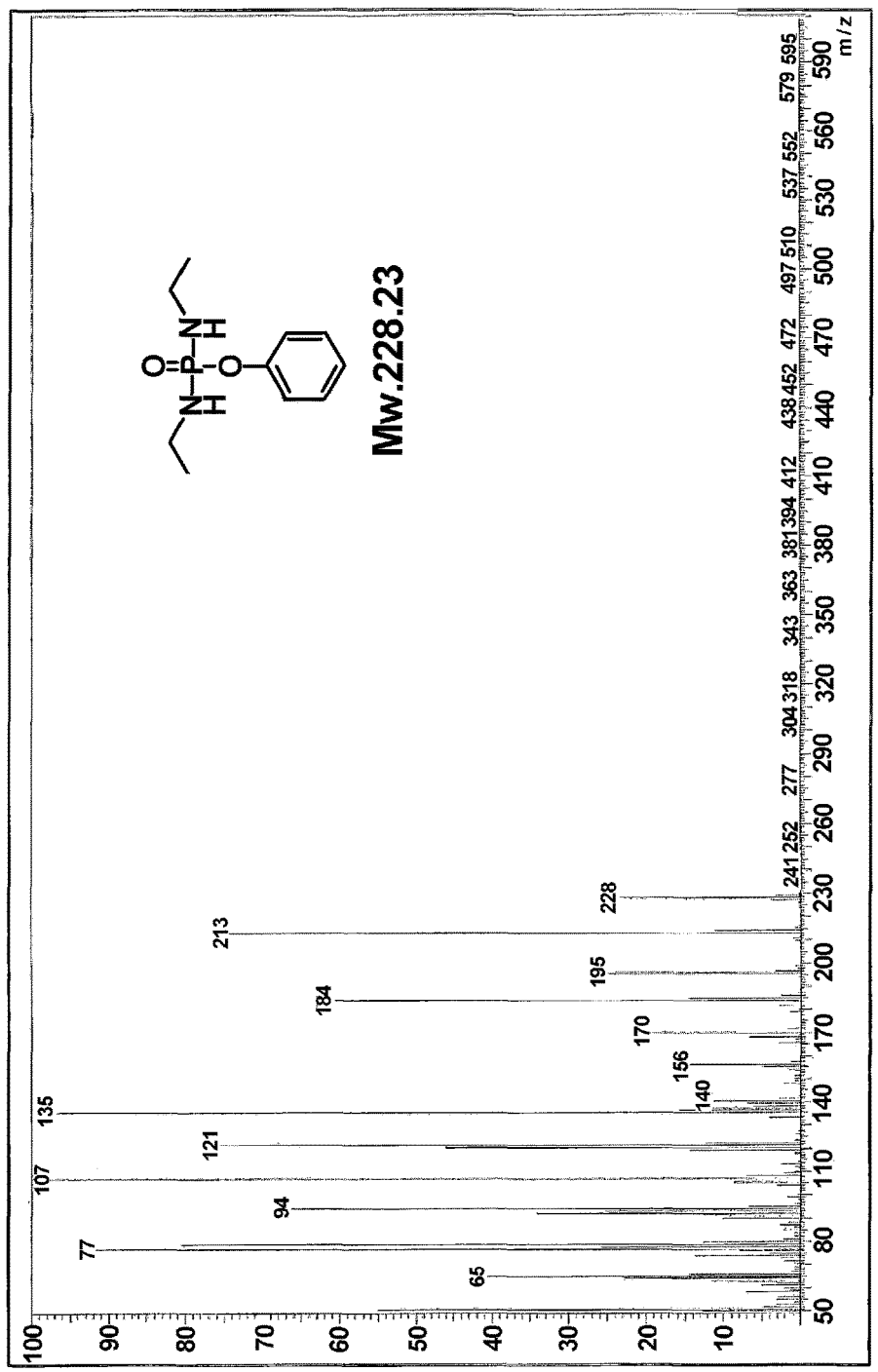

[Fig.7]
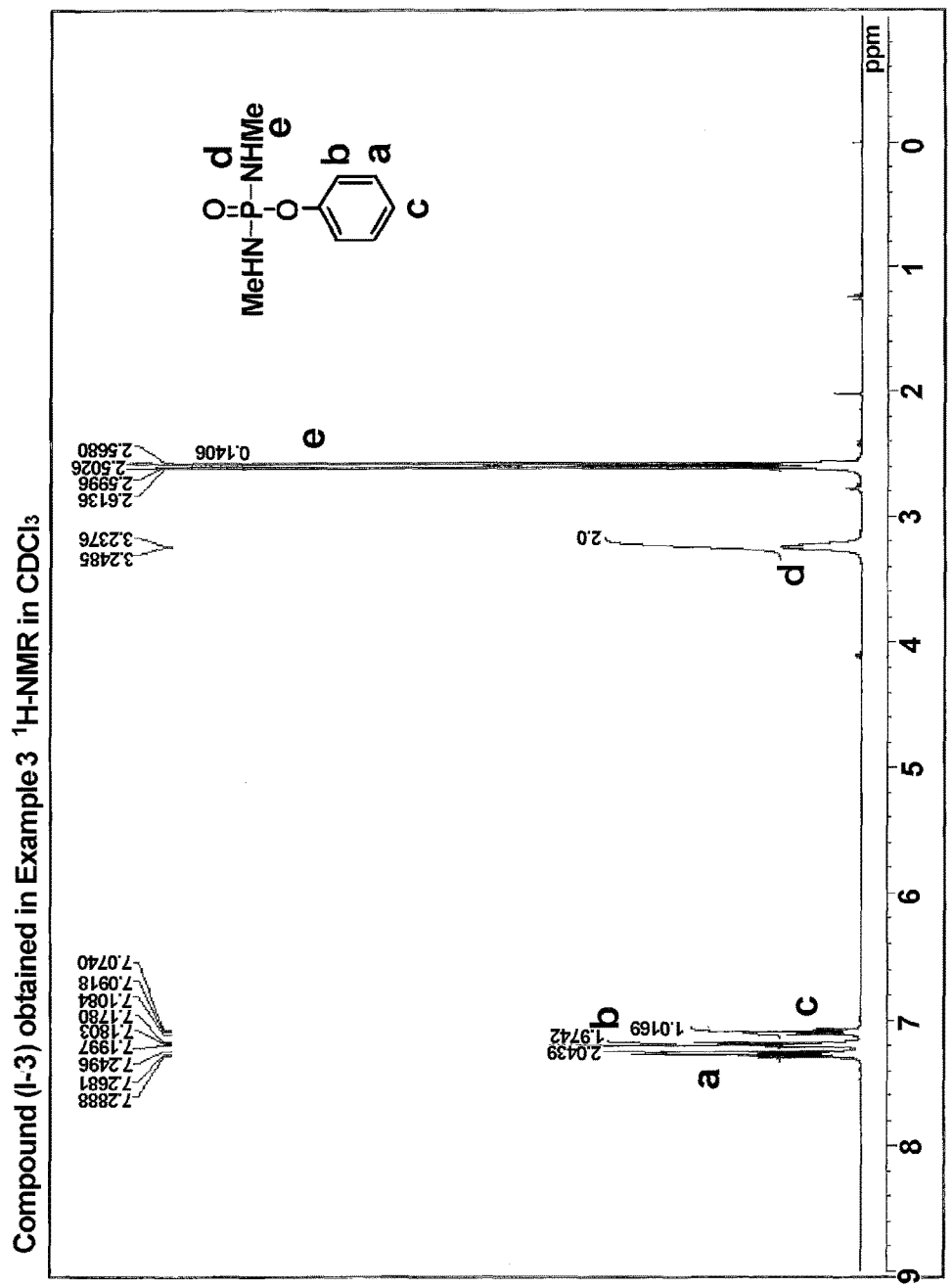

[Fig.8]
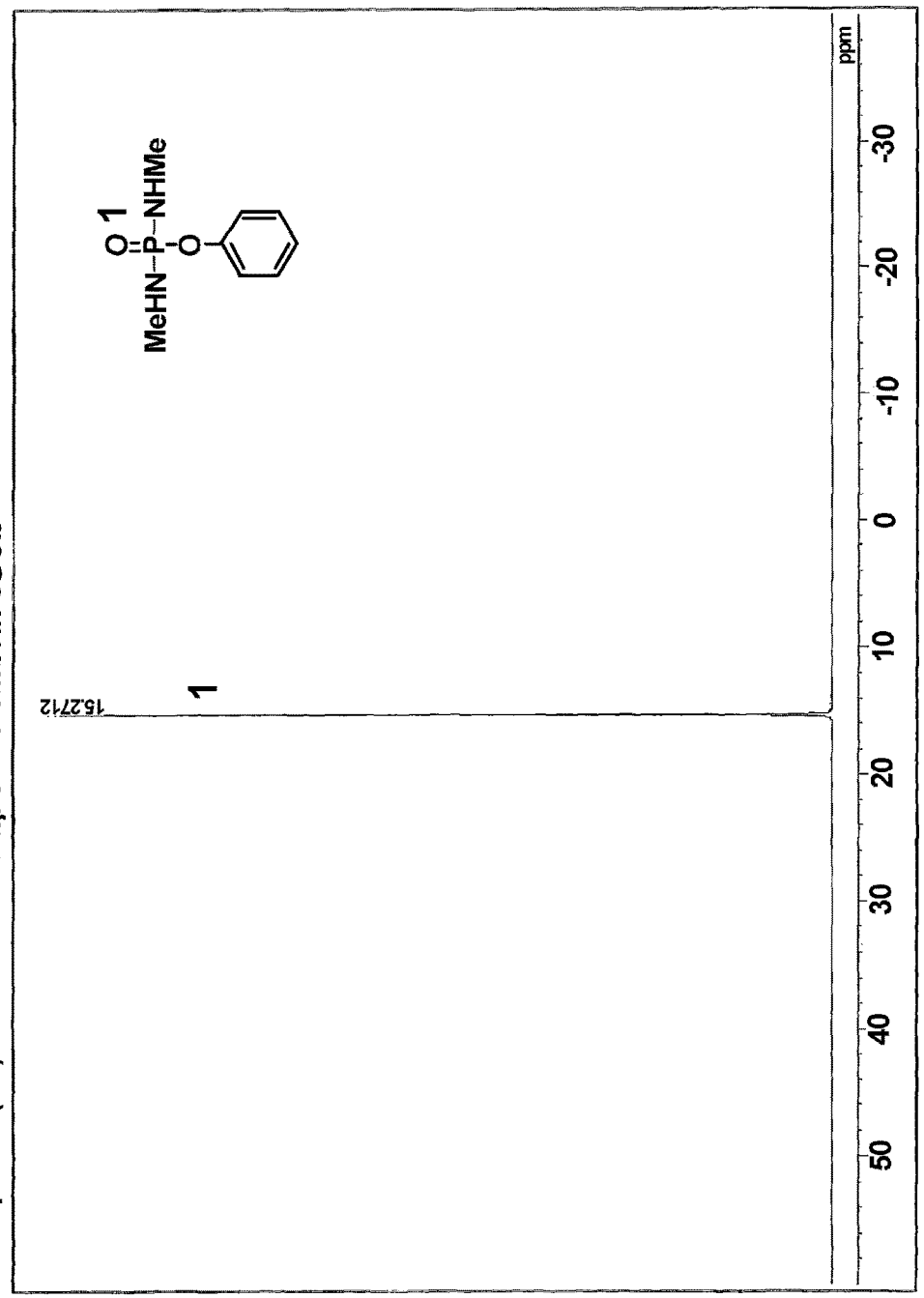

[Fig.9]
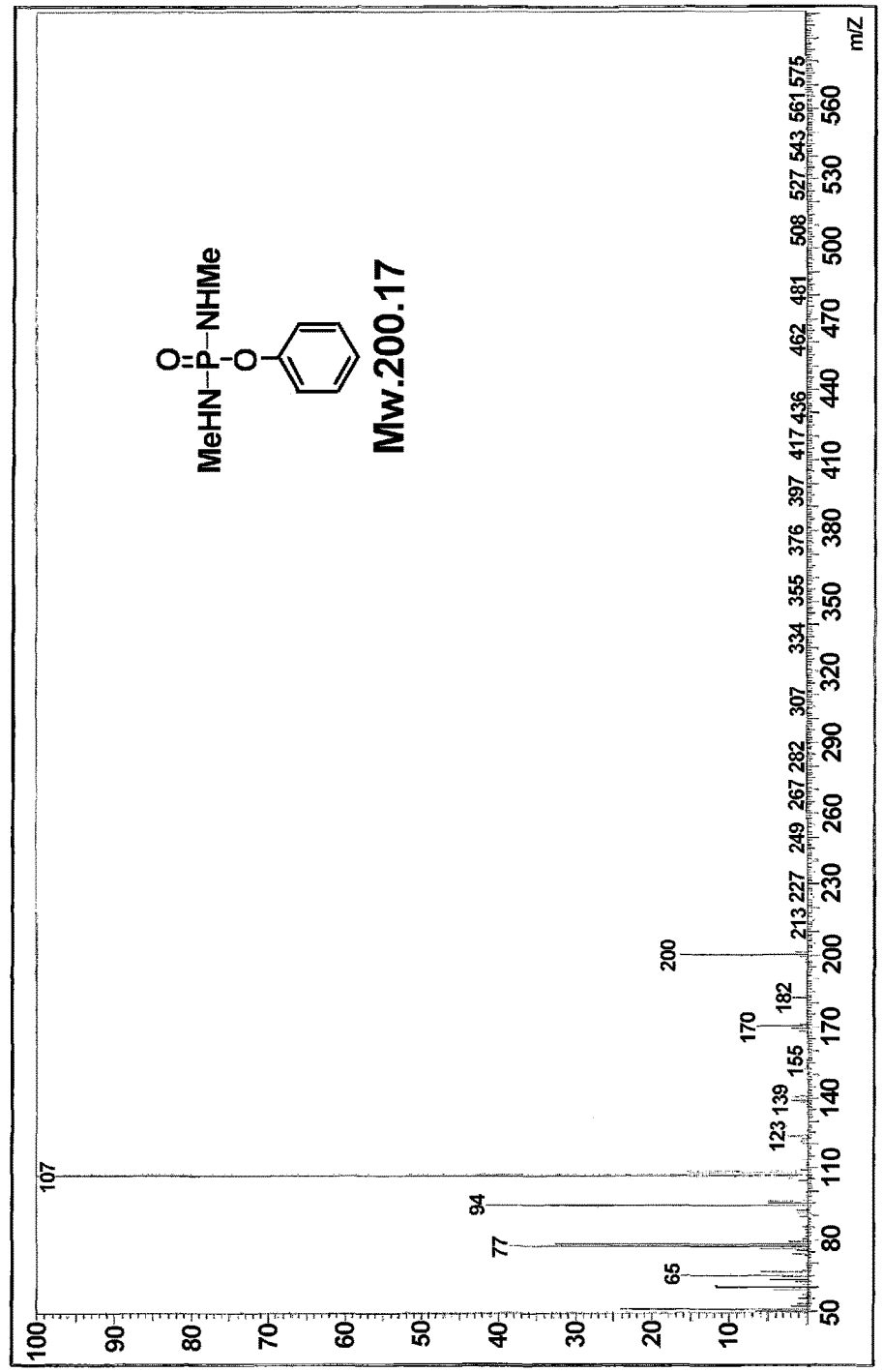

[Fig.10]
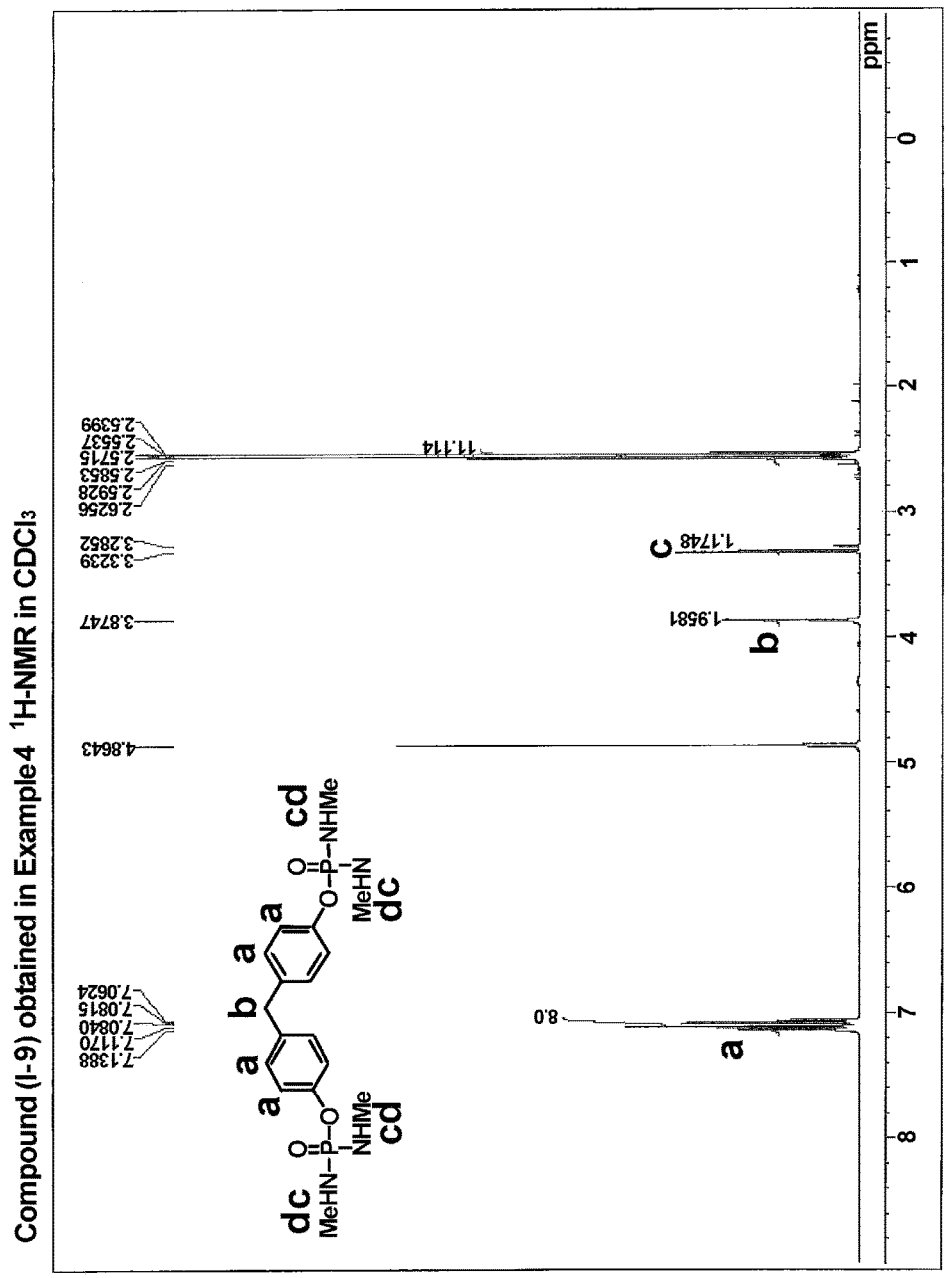

[Fig.11]
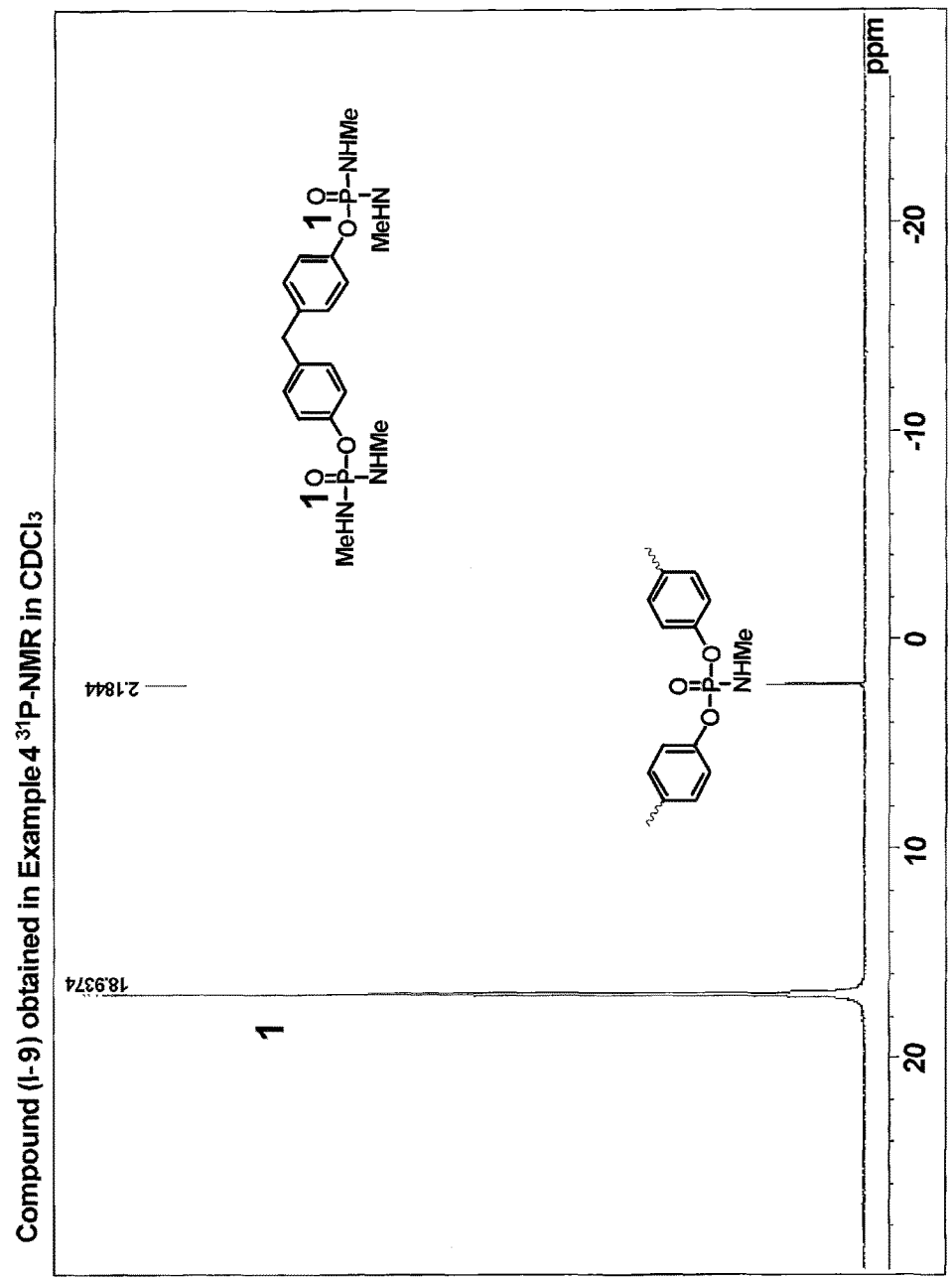

[Fig.12]
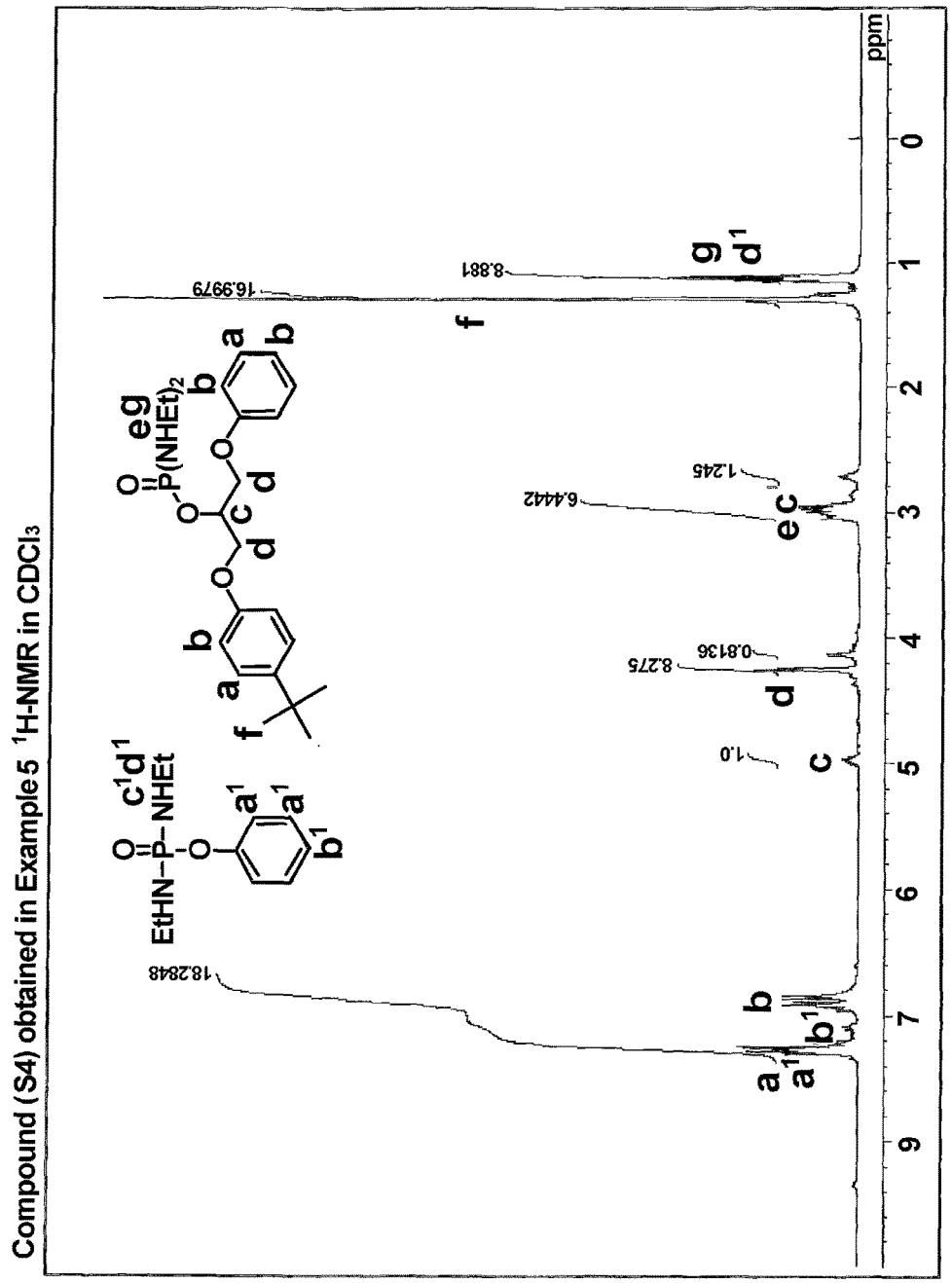

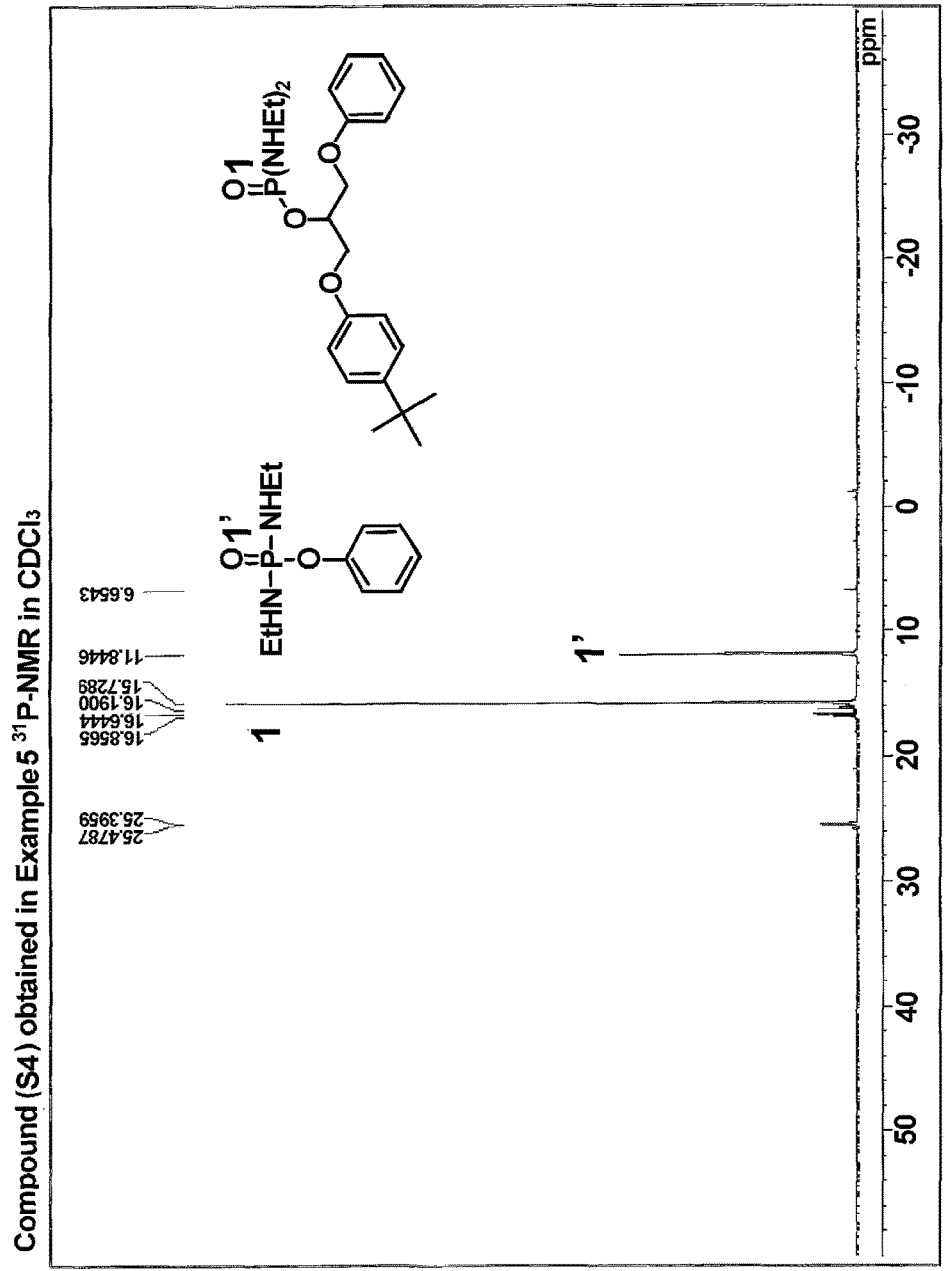

[Fig.14]
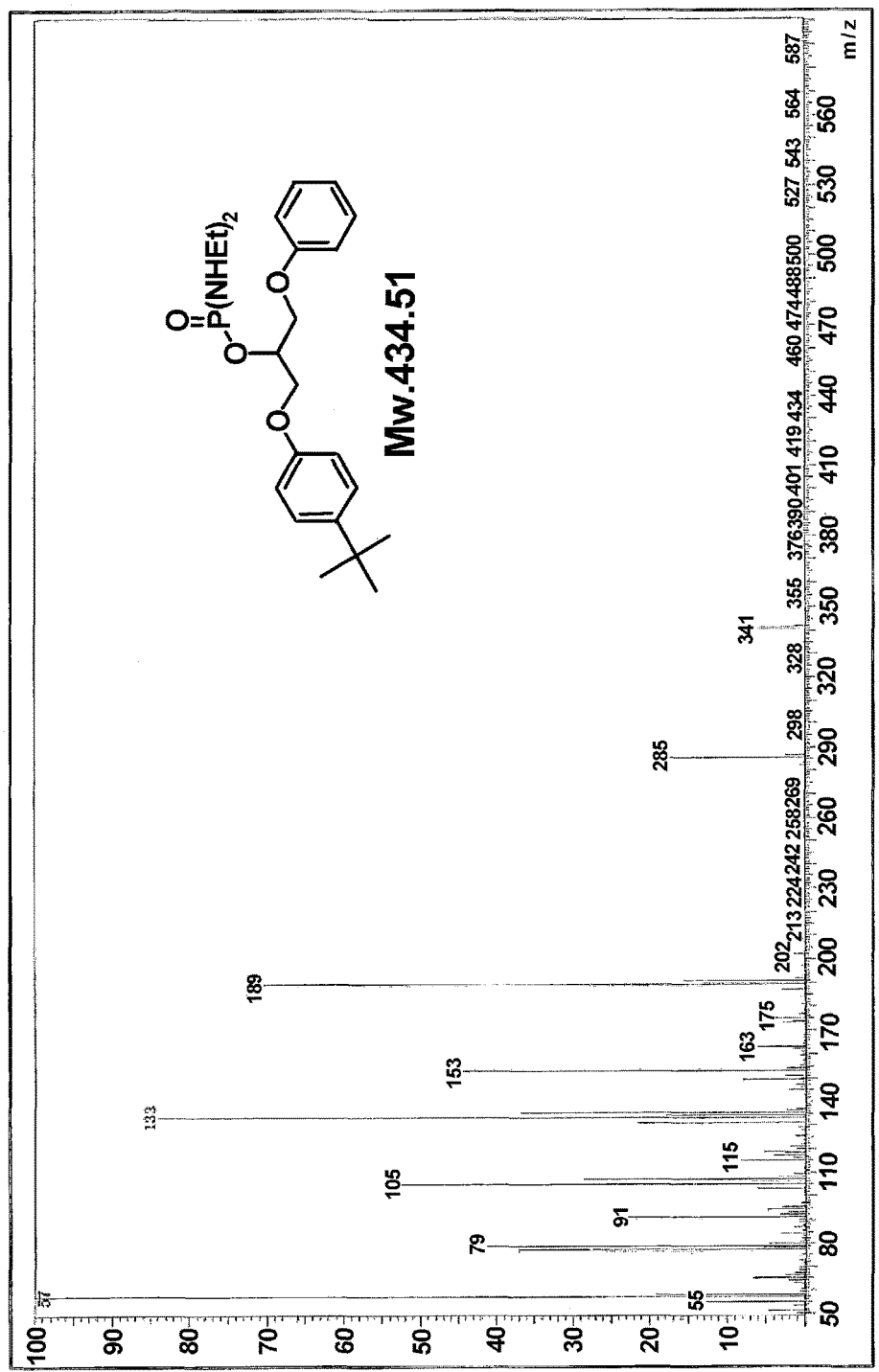

[Fig.15]
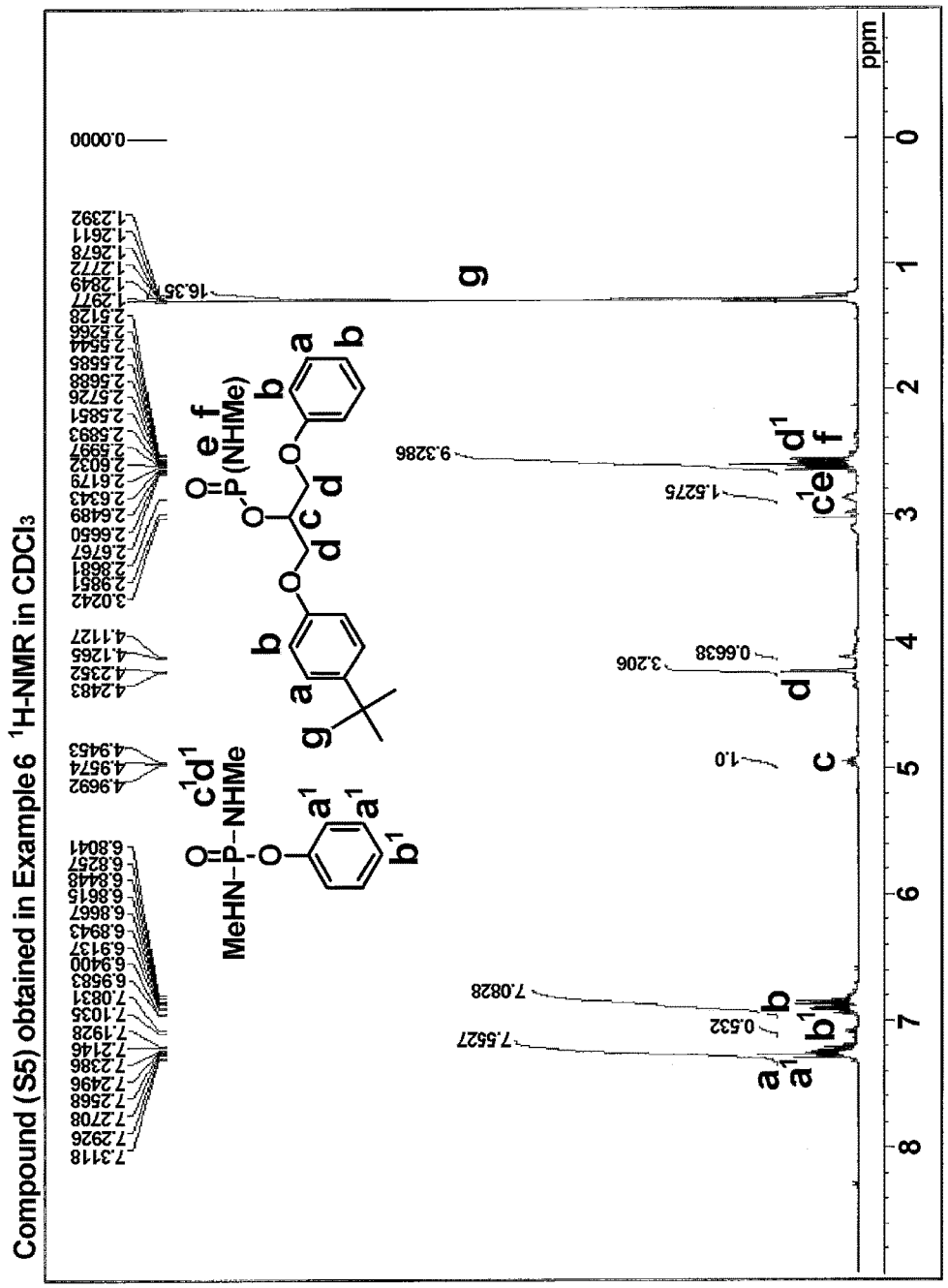

[Fig.16]
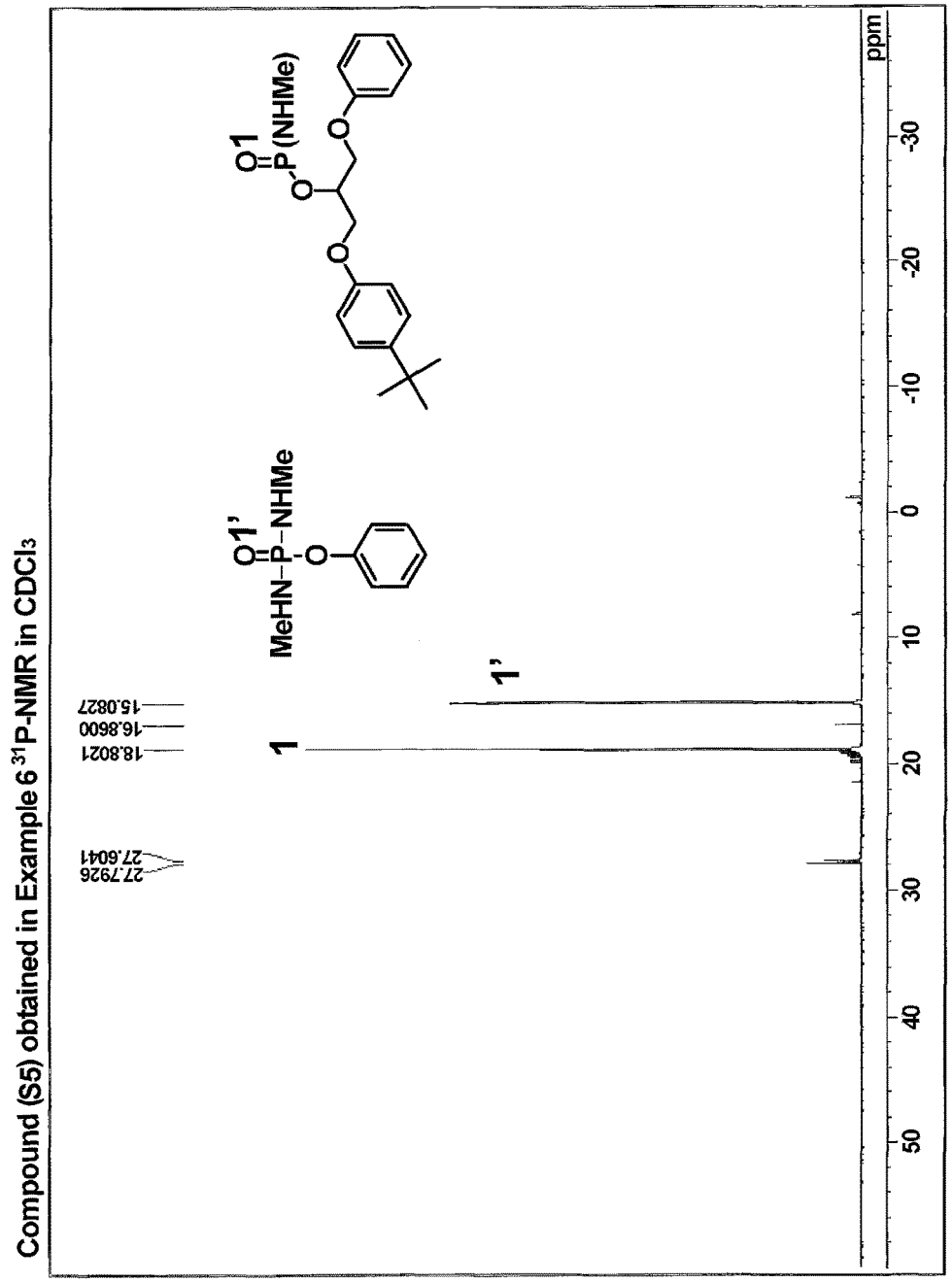

[Fig.17]
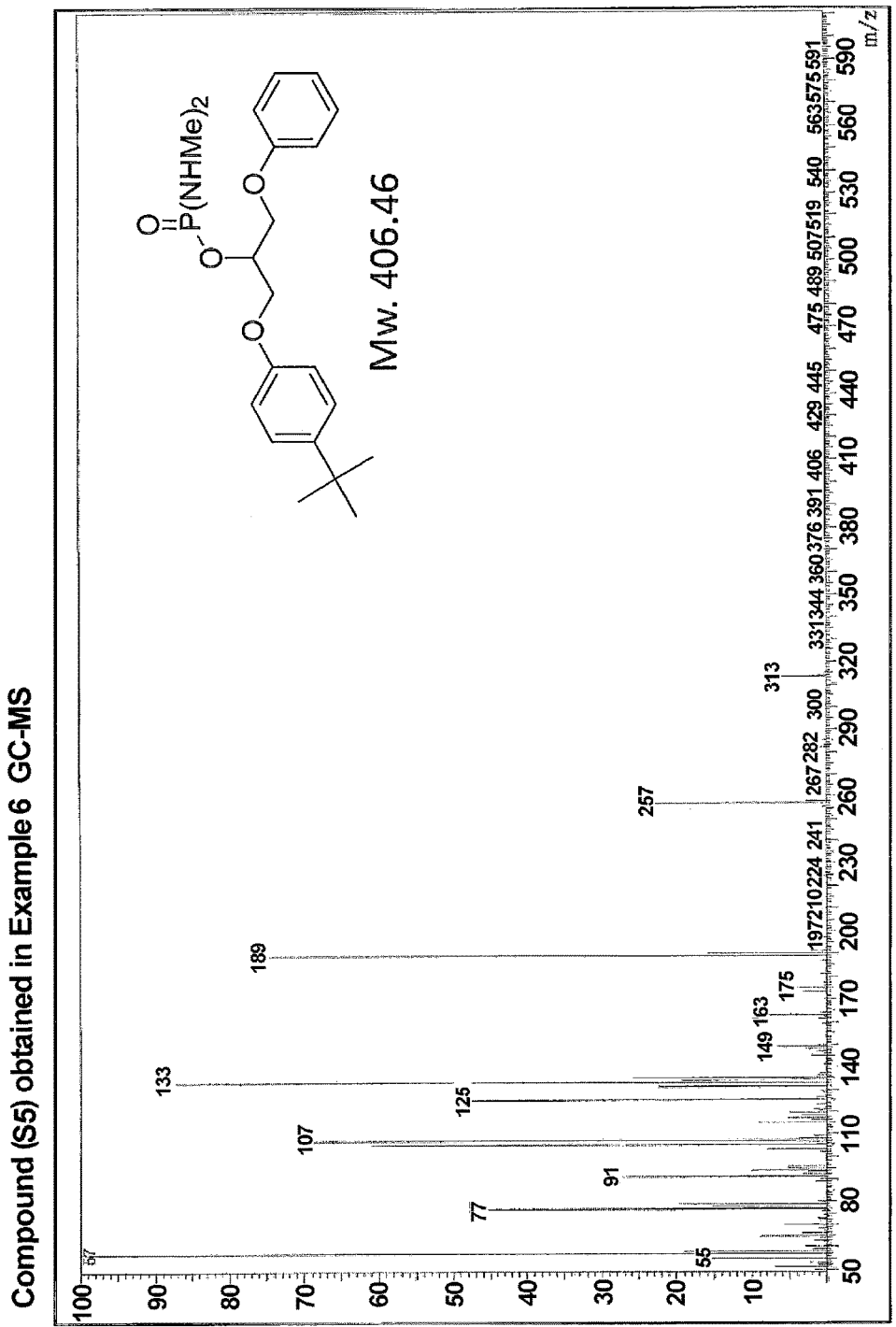

PHOSPHORUS-CONTAINING COMPOUND AND CURING EPOXY RESIN COMPOSITION CONTAINING SAME

TECHNICAL FIELD

This invention relates to a phosphorus-containing compound, particularly a reactive phosphorus-containing compound that can be combined with an epoxy compound to provide a curing epoxy resin composition expected to achieve flame retardation, reduction of dielectric constant, and the like.

BACKGROUND ART

The recent increase in concern with a global environmental problem and safety of the human body has boosted the demand for less hazard and more safety, as well as flame retardancy, of electric/electronic products. That is, reduction of harmful gas and smoke generation has been demanded.

Use of a bromine-containing flame retardant, which provides good flame retardancy, has been being limited on account of generation of toxic hydrogen halide gas (hydrogen bromide) on combustion. Therefore, studies have been directed to compositions containing an ordinary epoxy resin and a halogen-free flame retardant, such as a nitrogen compound, a phosphorus compound, or an inorganic compound. However, these additives for imparting flame retardancy are disadvantageous in that their flame retardant effect is insufficient or they adversely affect curing of the epoxy resin or are accompanied by reduction of physical properties, such as a glass transition temperature, of a cured product.

For example, triphenyl phosphate is widely used as a phosphorous-containing flame retardant for various resins. Patent Document 1 described below proposes adding a phosphorus-containing flame retardant composed of a high-molecular-weight divalent phenol and a phenol to an epoxy resin. Nevertheless, the proposed flame retardant should be used in a large quantity in order to impart sufficient flame retardancy to an epoxy resin. Adding a sufficient amount of the flame retardant to realize satisfactory flame retardation causes reduction in glass transition temperature, and reduction in amount of the flame retardant to be added in an attempt to increase the glass transition temperature results in insufficient flame retardancy. Patent Document 2 below proposes using a reactive phosphoric ester compound. The proposal has turned out to be impractical because incorporating the phosphoric ester compound into an epoxy resin makes the resin hygroscopic or makes part of the resin take on a three-dimensional structure, which increases the viscosity and thereby greatly reduces the workability of the resin composition.

CITATION LIST

Patent Document

Patent Document 1: JP 8-337709A
Patent Document 2: JP 10-195178A

SUMMARY OF THE INVENTION

Problem to be Solved by the Invention

An object of the invention is to provide a phosphorus-containing compound having reactivity with a glycidyl group, particularly a phosphorus-containing compound having glycidyl reactivity and therefore capable of providing a curing epoxy resin composition that is expected to achieve flame retardation, reduction of dielectric constant, and the like.

Means for Solving the Problem

As a result of extensive investigations, the inventors have found that a phosphorus-containing compound having a specific structure accomplishes the above object and reached the present invention.

The invention provides a phosphorus-containing compound represented by general formula (I):

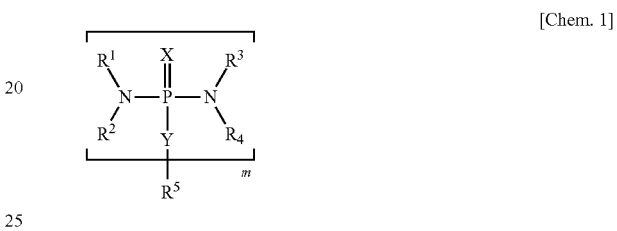

[Chem. 1]

wherein m represents a number of 1 to 10; $R^1$, $R^2$, $R^3$, and $R^4$ each independently represent a hydrogen atom, an alkyl group, or an aryl group; $R^5$ represents an alkyl group, an alkanediyl group, an alkanetriyl group, an alkanetetrayl group, or an aromatic group; X represents an oxygen atom or a sulfur atom; Y represents an oxygen atom, a sulfur atom, or =NR'; and R' represents a hydrogen atom, an alkyl group, or an aryl group.

The invention also provides a reaction process comprising causing the above-described phosphorus-containing compound to react with an epoxy compound according to the following reaction scheme:

[Chem. 1A]

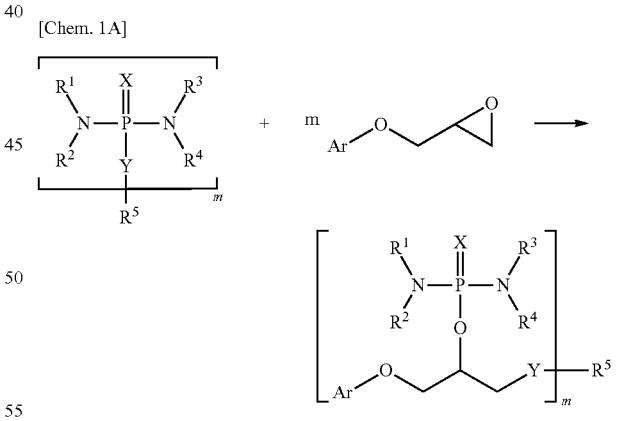

wherein m represents a number of 1 to 10; $R^1$, $R^2$, $R^3$, and $R^4$ each independently represent a hydrogen atom, an alkyl group, or an aryl group; $R^5$ represents an alkyl group, an alkanediyl group, an alkanetriyl group, an alkanetetrayl group, or an aromatic group; X represents an oxygen atom or a sulfur atom; Y represents an oxygen atom, a sulfur atom, or =$NR^6$; $R^6$ represents a hydrogen atom, an alkyl group, or an aryl group; and Ar represents an aromatic group.

The invention also provides an epoxy resin curing agent containing the above described phosphorus-containing compound.

The invention also provides a curing epoxy resin composition containing the epoxy resin curing agent.

Effect of the Invention

The invention provides a phosphorus-containing compound having excellent reactivity with an epoxy resin and promising to impart flame retardation to the epoxy resin and to reduce the dielectric constant of the epoxy resin.

BRIEF DESCRIPTION OF THE ACCOMPANYING DRAWINGS

FIG. 1 is a $^1$H-NMR spectrum of the phosphorus-containing compound (I-1) obtained in Example 1.

FIG. 2 is a $^{31}$P-NMR spectrum of the phosphorus-containing compound (I-1) obtained in Example 1.

FIG. 3 is a GC-MS spectrum of the phosphorus-containing compound (I-1) obtained in Example 1.

FIG. 4 is a $^1$H-NMR spectrum of the phosphorus-containing compound (I-2) obtained in Example 2.

FIG. 5 is a $^{31}$P-NMR spectrum of the phosphorus-containing compound (I-2) obtained in Example 2.

FIG. 6 is a GC-MS spectrum of the phosphorus-containing compound (I-2) obtained in Example 2.

FIG. 7 is a $^1$H-NMR spectrum of the phosphorus-containing compound (I-3) obtained in Example 3.

FIG. 8 is a $^{31}$P-NMR spectrum of the phosphorus-containing compound (I-3) obtained in Example 3.

FIG. 9 is a GC-MS spectrum of the phosphorus-containing compound (1-3 obtained in Example 3.

FIG. 10 is a $^1$H-NMR spectrum of the phosphorus-containing compound (I-9) obtained in Example 4.

FIG. 11 is a $^{31}$P-NMR spectrum of the phosphorus-containing compound (I-9) obtained in Example 4.

FIG. 12 is a $^1$H-NMR spectrum of S4 obtained in Example 5.

FIG. 13 is a $^{31}$P-NMR spectrum of S4 obtained in Example 5.

FIG. 14 is a GC-MS spectrum of S4 obtained in Example 5.

FIG. 15 is a $^1$H-NMR spectrum of S5 obtained in Example 6.

FIG. 16 is a $^{31}$P-NMR spectrum of S5 obtained in Example 6.

FIG. 17 is a GC-MS spectrum of S5 obtained in Example 6.

BEST MODE FOR CARRYING OUT THE INVENTION

The invention will be described based on its preferred embodiments. The phosphorus-containing compound according to the invention is a novel compound represented by general formula (I) and has a reactive group with a glycidyl group in its structure.

Examples of the alkyl group as represented by $R^1$, $R^2$, $R^3$, $R^4$, and R' (when Y is =NR') in general formula (I) include those having 1 to 10 carbon atoms, such as methyl, ethyl, propyl, isopropyl, butyl, isobutyl, tert-butyl, amyl, isoamyl, tert-amyl, hexyl, isohexyl, octyl, 2-ethylhexyl, tert-octyl, nonyl, and decyl. Examples of the aryl group as represented by $R^1$, $R^2$, $R^3$, $R^4$, and R' (when Y is =NR') include those having 6 to 12 carbon atoms, such as phenyl and naphthyl. $R^1$, $R^2$, $R^3$, and $R^4$ are each preferably an alkyl group having 1 to 5 carbon atoms.

Examples of the alkyl group as represented by $R^5$ include those having 1 to 10 carbon atoms, such as methyl, ethyl, propyl, isopropyl, butyl, isobutyl, tert-butyl, amyl, isoamyl, tert-amyl, hexyl, isohexyl, octyl, 2-ethylhexyl, tert-octyl, nonyl, and decyl. Examples of the alkanediyl group as $R^5$ include those having 1 to 10 carbon atoms, such as methylene, ethylene, propylene, butylene, and octylene. Examples of the alkanetriyl group as $R^5$ include those having 1 to 6 carbon atoms, such as methylenetriyl and 1,1,3-ethylenetriyl. The alkanetetrayl as $R^5$ is exemplified by those having 2 to 6 carbon atoms, such as 1,1,2,2-ethylenetriyl.

Examples of the aromatic group as represented by $R^5$ include those derived from mononuclear polyhydric phenol compounds, such as hydroquinone, resorcin, pyrocatechol, and phloroglucinol, and those derived from polynuclear polyhydric phenol compounds, such as dihydroxynaphthalene, biphenol, methylenebisphenol (bisphenol F), methylenebis(o-cresol), ethylidenebisphenol, isopropylidenebisphenol (bisphenol A), isopropylidenebis(o-cresol), tetrabromobisphenol A, 1,3-bis(4-hydroxycumylbenzene), 1,4-bis(4-hydroxycumylbenzene), 1,1,3-tris(4-hydroxyphenyl)butane, 1,1,2,2-tetra(4-hydroxyphenyl)ethane, thiobisphenol, sulfonylbisphenol, oxybisphenol, phenol novolak, o-cresol novolak, ethylphenol novolak, butylphenol novolak, octylphenol novolak, resorcin novolak, and terpene phenol. Preferred of them are groups represented by the formulae (1) through (9) shown below.

[Chem. 2]

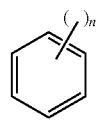

(1)

wherein n represents an integer of 1 to 4,

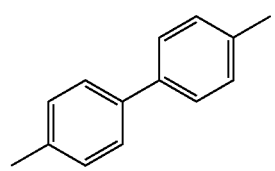

(2)

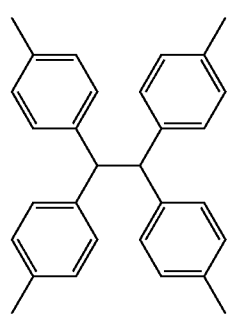

(3)

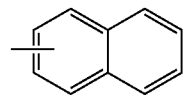

(4)

-continued

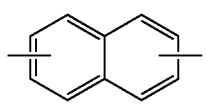
(5)

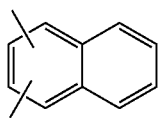
(6)

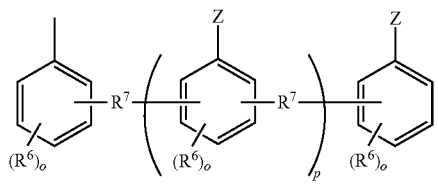
(7)

wherein R⁶ represents a hydrogen atom or an alkyl group having 1 to 4 carbon atoms; o represents an integer of 1 to 3; p represents an integer of 0 to 50;
Z represents —OH  or  (i)

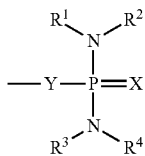
(ii)

wherein R¹, R², R³, R⁴, X, and Y are as defined above; R⁷ represents

(iii)

wherein R⁸ and R⁹ each represent a hydrogen atom, CH₃, or CF₃,

(iv)

(v)

(vi)

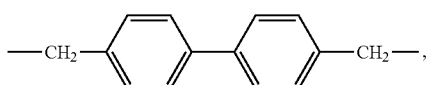
(vii)

(viii)

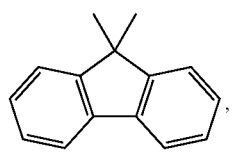
(ix)

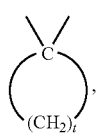
(x)

wherein t represents an integer of 4 to 12,

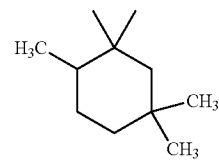
(xi)

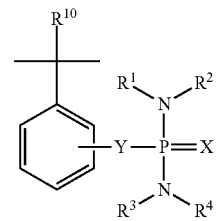
(xii)

wherein R¹⁰ represents a hydrogen atom or CH₃; and R¹, R², R³, R⁴, X, and Y are as defined above,

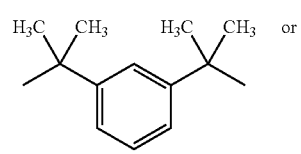
(xiii)

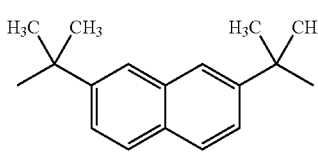
(xiv)

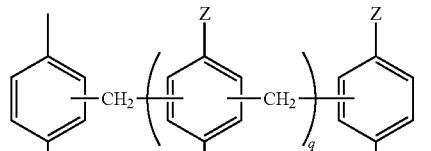

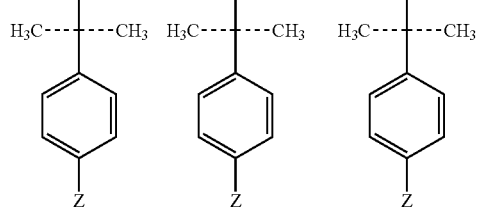
(8)

wherein q represents an integer of 0 to 50, and Z is as defined above, and

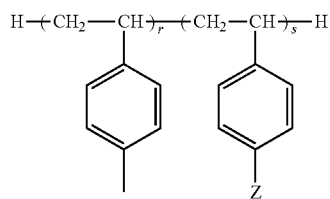

(9)

wherein r represents an integer of 0 to 25, and s represents an integer of 0 to 25, provided that the sum of r and s is 5 to 50; and Z is as defined above.

Specific examples of the phosphorus-containing compound of the invention include those represented by formulae (I-1) through (I-9):

[Chem. 3]

(I-1)

[Chem. 4]

(I-2)

[Chem. 5]

(I-3)

[Chem. 6]

(I-4)

[Chem. 7]

(I-5)

[Chem. 8]

(I-6)

[Chem. 9]

(I-7)

[Chem. 10]

(I-8)

[Chem. 10A]

(I-9)

Of the phosphorus-containing compounds of the invention preferred are those of general formula (I) in which $R^1$, $R^2$, $R^3$, and $R^4$ each independently represent a C1-C5 alkyl group; $R^5$ represents the aromatic group represented by the formulae (1) to (9); and X and Y are each oxygen in terms of phosphorus content and ready availability of starting materials used to synthesize the compound.

The phosphorus-containing compound of the invention can be prepared by a method shown by the following reaction scheme (A) or (B):

[Chem. 11]

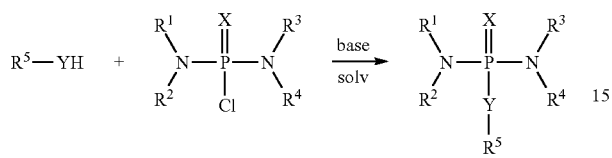

(A)

wherein $R^1$, $R^2$, $R^3$, $R^4$, $R^5$, X, and Y are as defined above.

[Chem. 11A]

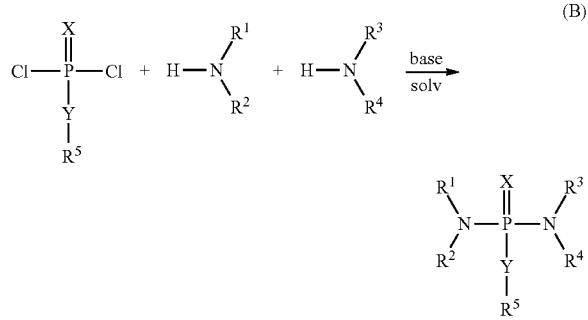

(B)

wherein $R^1$, $R^2$, $R^3$, $R^4$, $R^5$, X, and Y are as defined above.

Examples of the base that can be used in the above reactions include tertiary amines, such as triethylamine, tributylamine, diazabicycloundecene, diazabicyclononene, and 1,4-diazabicyclo[2.2.2]octane; pyridines, such as pyridine and N,N-dimethylaminopyridine; imidazoles, such as 1-methylimidazole; and phosphines, such as triphenylphosphine, tributylphosphine, and tricyclohexylphosphine.

Examples of the solvent that can be used in the above reactions include ketones, such as methyl ethyl ketone, methyl amyl ketone, diethyl ketone, acetone, methyl isopropyl ketone, propylene glycol monomethyl ether acetate, and cyclohexanone; ethers, such as tetrahydrofuran, 1,2-dimethoxyethane, 1,2-diethoxyethane, and propylene glycol monomethyl ether; esters, such as ethyl acetate and n-butyl acetate; aromatic hydrocarbons, such as benzene, toluene, and xylene; halogenated aliphatic hydrocarbons, such as carbon tetrachloride, chloroform, trichloroethylene, and methylene chloride; and halogenated aromatic hydrocarbons, such as chlorobenzene.

The reactions shown above are carried out at a temperature of −80° to 100° C., preferably room temperature to 50° C., for a period of 0.5 to 72 hours, preferably 1 to 24 hours.

The phosphorus-containing compound of the invention efficiently reacts with an epoxy compound according to the following reaction scheme and is suitably used as an epoxy resin curing agent.

[Chem. 11B]

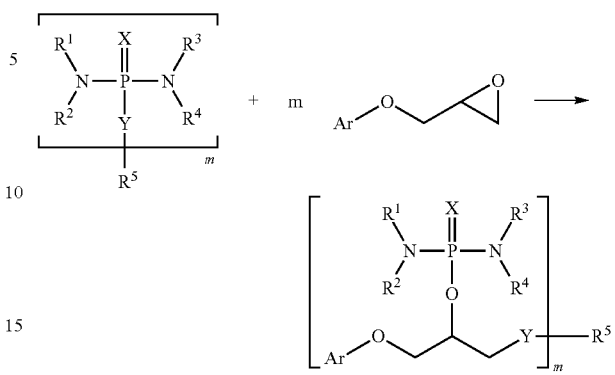

wherein m represents a number of 1 to 10; $R^1$, $R^2$, $R^3$, and $R^4$ each independently represent a hydrogen atom, an alkyl group, or an aryl group; $R^5$ represents an alkyl group, an alkanediyl group, an alkanetriyl group, an alkanetetrayl group, or an aromatic group; X represents an oxygen atom or a sulfur atom; Y represents an oxygen atom, a sulfur atom, or =$NR^6$; $R^6$ represents a hydrogen atom, an alkyl group, or an aryl group; and Ar represents an aromatic group.

Examples of the aromatic group as represented by Ar in the above reaction formula include the aryl groups as represented by $R^1$ and so on and the aromatic groups as represented by $R^5$ as described with reference to the general formula (I).

The epoxy resin curing agent of the invention comprises at least one of the phosphorus-containing compounds of the invention. That is, the phosphorus-containing compounds of the invention can be used as an epoxy resin curing agent either individually or in combination with one another. The epoxy resin curing agent of the invention may comprise known epoxy resin curing agents in addition to the phosphorus-containing compound of the invention. Useful known epoxy resin curing agents include general-purpose epoxy resin curing agents that will hereinafter be described for use in the curing epoxy resin composition of the invention. The known epoxy resin curing agents may be used as a mixture of two or more thereof.

The content of the phosphorus-containing compound of the invention in the epoxy resin curing agent of the invention is preferably 5% to 100% by mass, more preferably 20% to 100% by mass.

The curing epoxy resin composition according to the invention comprises an epoxy compound (epoxy resin) and the epoxy resin curing agent containing the phosphorus-containing compound of the invention.

Examples of the epoxy compound that can be used in the curing epoxy resin composition of the invention include polyglycidyl ether compounds of mononuclear polyhydric phenol compounds, such as hydroquinone, resorcinol, pyrocatechol, and phloroglucinol; polyglycidyl ether compounds of polynuclear polyhydric phenol compounds, such as dihydroxynaphthalene, biphenol, methylenebisphenol (bisphenol F), methylenebis(o-cresol), ethylidene bisphenol, isopropylidene bisphenol (bisphenol A), isopropylidene bis(o-cresol), tetrabromobisphenol A, 1,3-bis(4-hydroxycumylbenzene), 1,4-bis(4-hydroxycumylbenzene), 1,1,3-tris(4-hydroxyphenyl)butane, 1,1,2,2-tetra(4-hydroxyphenyl)ethane, thiobisphenol, sulfonylbisphenol, oxybisphenol, phenol novolak, o-cresol novolak, ethylphenol novolak, butylphenol novolak, octylphenol novolak, resorcin novolak, and terpene phenol; polyglycidyl ethers of polyhydric alcohols, such as ethylene glycol, propylene glycol, butylene glycol, hexanediol, polyethylene glycol, thiodiglycol, glycerol, trimethylolpropane, pentaerythritol, sorbitol, and bisphenol A-ethylene oxide adduct; homopolymers or copolymers of glycidyl methacrylate or a glycidyl ester of an aliphatic, aromatic or alicyclic polybasic acid, such as maleic acid, fumaric acid, itaconic acid, succinic acid, glutaric acid, suberic acid, adipic acid, azelaic acid, sebacic acid, dimer acid, trimer acid, phthalic acid, isophthalic acid, terephthalic acid, trimellitic acid, trimesic acid, pyromellitic acid, tetrahydrophthalic acid, hexahydrophthalic acid, or endomethylene tetrahydrophthalic acid; epoxy compounds having a glycidylamino group, such as N, N-diglycidylaniline, bis(4-(N-methyl-N-glycidylamino) phenyl)methane, and diglycidyl o-toluidine; epoxidized cyclic olefin compounds, such as vinylcyclohexene diepoxide, dicyclopentanediene diepoxide, 3,4-epoxycyclohexyl-methyl-3,4-epoxycyclohexane carboxylate, 3,4-epoxy-6-methylcyclohexylmethyl-6-methylcyclohexane carboxylate, and bis(3,4-epoxy-6-methylcyclohexylmethyl) adipate; epoxidized conjugated diene polymers, such as epoxidized polybutadiene and an epoxidized styrene-butadiene copolymer; and heterocyclic compounds, such as triglycidyl isocyanurate. These epoxy compounds may be internally crosslinked by a prepolymer of the terminal isocyanate or may have their molecular weight increased by a polyvalent active hydrogen compound (e.g., polyhydric phenols, polyamines, carbonyl-containing compounds, and polyphosphoric esters).

The epoxy compound preferably has an epoxy equivalent of from 70 to 3,000, more preferably 90 to 2,000. With an epoxy equivalent less than 70, the physical properties of the cured product can reduce. With an epoxy equivalent larger than 3,000, curability can be insufficient.

The curing epoxy resin composition preferably contains 0.1 to 5 equivalents, more preferably 1 to 3 equivalents, of the epoxy compound per equivalent of the phosphorus-containing compound of the invention.

The curing epoxy resin composition of the invention is preferably combined with a curing catalyst, such as p-dimethylaminopyridine, triphenylphosphine, imidazole, tertiary amines, phosphines, quaternary ammonium salts, and quaternary phosphonium salts.

The curing epoxy resin composition of the invention is preferably combined with a general-purpose epoxy resin curing agent. Suitable epoxy resin curing agents include imidazoles, such as 2-ethyl-4-methylimidazole, 1,2-dimethylimidazole, and 1-(2-methylimidazol-1-ylmethyl)naphthalen-2-ol; polyalkylpolyamines, such as diethylenetriamine, triethylenetetramine, and tetraethylenepentamine; alicyclic polyamines, such as 1,2-diaminocyclohexane, 1,4-diamino-3,6-diethylcyclohexane, and isophoronediamine; and aromatic polyamines, such as m-xylylenediamine, diaminodiphenylmethane, and diaminodiphenyl sulfone. Further included are polyepoxy adducts of these polyamines obtained by the reaction with various epoxy resins, such as glycidyl ethers (e.g., phenyl glycidyl ether, butyl glycidyl ether, bisphenol A diglycidyl ether, and bisphenol F glycidyl ether) or carboxylic acid glycidyl esters in a usual manner; amide-modified products of the organic polyamines obtained by the reaction with carboxylic acids (e.g., phthalic acid, isophthalic acid, and dimer acid) in a usual manner; and Mannich-modified products of the polyamines obtained by the reaction with aldehydes (e.g., formaldehyde) and phenols having at least one aldehyde-reactive site on their nucleus (e.g., phenol, cresol, xylenol, tert-butylphenol, and resorcinol) in a usual manner. Furthermore, latent curing agents, such as dicyandiamides, acid anhydrides, and imidazoles, are also useful.

If necessary, the curing epoxy resin composition of the invention may contain commonly used additives, including reactive or nonreactive diluents (plasticizers), such as monoglycidyl ethers, dioctyl phthalate, dibutyl phthalate, benzyl alcohol, and coal tar; fillers or pigments, such as glass fiber, carbon fiber, cellulose, silica sand, cement, kaolin, clay, aluminum hydroxide, bentonite, talc, silica, finely divided silica, titanium dioxide, carbon black, graphite, iron oxide, and bituminous materials; silane coupling agents, such as γ-aminopropyltriethoxysilane, N-β-(aminoethyl)-γ-aminopropyltriethoxysilane, N-β-(aminoethyl)-N'β-(aminoethyl)-γ-aminopropyltriethoxysilane, γ-anilinopropyltriethoxysilane, γ-glycidoxypropyltriethoxysilane, β-(3,4-epoxycyclohexyl)ethyltriethoxysilane, vinyl triethoxysilane, N-β-(N-vinylbenzylaminoethyl)-γ-aminopropyltriethoxysilane, γ-methacryloxypropyltrimethoxysilane, γ-chloropropyltrimethoxy silane, and γ-mercaptopropyltrimethoxysilane; lubricants, such as candelilla wax, carnauba wax, Japan wax, insect wax, beeswax, lanolin, spermaceti wax, montan wax, petroleum wax, aliphatic wax, aliphatic esters, aliphatic ethers, aromatic esters, and aromatic ethers; thickeners; thixotropic agents; antioxidants; light stabilizers; UV absorbers; flame retardants; defoamers; rust inhibitors; colloidal silica, and colloidal alumina. Adhesive resins, such as xylene resin and petroleum resins, may be used in combination.

The curing epoxy resin composition of the invention can be used for a wide range of applications, such as coatings or adhesives for concrete, cement mortar, various metals, leather, glass, rubber, plastics, wood, cloth, and paper; pressure-sensitive adhesives for packaging adhesive tape, adhesive labels, labels for frozen foods, removable labels, labels for POS system, adhesive wallpaper, and adhesive flooring; processed paper, such as art paper, light-weight coated paper, cast-coated paper, coated paperboard, carbonless copy paper, and impregnated paper; textile processing agents, such as sizing agents, anti-fray agents, and processing agents for natural fibers, synthetic fibers, glass fiber, carbon fiber, and metal fibers; building materials, such as sealants, cement admixtures, and waterproof materials; and sealants for electronic/electric devices.

EXAMPLES

The invention will now be illustrated in greater detail, but it should be understood that the invention is not deemed to be limited thereto.

Example 1

Synthesis of Phosphorus-Containing Compound [I-1]

A 100 ml three-necked flask equipped with a rotor, a reflux tube, and a rubber septum was charged with 0.1 g (1 mmol) of 4-dimethylaminopyridine (DMAP). After thoroughly drying and purging with nitrogen, the flask was charged with 0.9 g (10 mmol) of phenol and 10 ml of ultra-dehydrated tetrahydrofuran using a syringe. To the mixture was added dropwise 2.0 g (12 mmol) of bis(dimethylamino)phosphoryl chloride using a syringe taking care so that the reaction temperature did not exceed 30° C. After completion of the addition, the reaction system was stirred for 10 minutes. To the reaction solution were added 1.2 g (12 mmol) of triethylamine using a syringe taking care not to let the reaction temperature exceed 40° C., followed by stirring overnight. To the reaction mixture were added 5 ml of a saturated ammonium chloride aqueous solution and 5 ml of water, followed by stirring well. The solution was transferred to a separatory funnel, extracted 3 times with 10 ml portions of diethyl ether to obtain an organic layer. The organic layer was washed with 10 ml of water and dried over anhydrous magnesium sulfate. The solvent was removed using an evaporator to give pale yellow liquid (crude yield: 93.3%, GC purity: 70.5%). The crude product was purified by column chromatography (stationary phase: silica gel, mobile phase: ethyl acetate/hexane=2/1 by volume, Rf=0.20) to give the desired phosphorus-containing compound [I-1] as colorless liquid (overall yield: 44.0%, GC purity: >99%, $^{31}$P-NMR: 15.94 ppm). The results of the identification analyses are shown in FIG. 1 ($^1$H-NMR), FIG. 2 ($^{31}$P-NMR), and FIG. 3 (GC-MS).

Example 2

Synthesis of Phosphorus-Containing Compound [I-2]

A 100 ml three-necked flask equipped with a rotor, a reflux tube, and a rubber septum was thoroughly dried, purged with nitrogen, and charged with 9.5 g (21 mmol) of an ethylamine tetrahydrofuran solution, 2.1 g (21 mmol) of triethylamine, and 5 ml of ultra-dehydrated tetrahydrofuran while cooling in a salt-ice-water bath. After stirring the mixture for 5 minutes, 2.1 g (10 mmol) of phenyl dichlorophosphate was added thereto dropwise using a syringe taking care not to let the reaction temperature exceed 0° C. After completion of the addition, the reaction system was stirred for 1 hour. The salt-ice-water bath was removed, and the reaction system was stirred at room temperature overnight. To the reaction solution were added 5 ml of a saturated ammonium chloride aqueous solution and 5 ml of water, followed by stirring well. The solution was transferred to a separatory funnel, extracted 3 times with 10 ml portions of ethyl acetate to obtain an organic layer. The organic layer was washed with 10 ml of water and dried over anhydrous magnesium sulfate. The solvent was removed in an evaporator to give pale yellow liquid (crude yield: 92.9%, GC purity: 98.5%). The crude product was purified by column chromatography (stationary phase: silica gel, mobile phase: ethyl acetate, Rf=0.23) to give the desired phosphorus-containing compound [I-2] as colorless liquid (overall yield: 73.8%; GC purity: >99%, $^{31}$P-NMR: 12.01 ppm). The results of the identification analyses are shown in FIG. 4 ($^1$H-NMR), FIG. 5 ($^{31}$P-NMR), and FIG. 6 (GC-MS).

Example 3

Synthesis of Phosphorus-Containing Compound [I-3]

A 100 ml three-necked flask equipped with a rotor, a reflux tube, and a rubber septum was thoroughly dried, purged with nitrogen, and charged with 9.0 g (21 mmol) of a methylamine tetrahydrofuran solution, 2.1 g (21 mmol) of triethylamine, and 5 ml of ultra-dehydrated tetrahydrofuran while cooling in a salt-ice-water bath. After stirring the mixture for 5 minutes, 2.1 g (10 mmol) of phenyl dichlorophosphate were added thereto dropwise using a syringe taking care not to let the reaction temperature exceed 0° C. After completion of the addition, the reaction system was stirred for 1 hour. The salt-ice-water bath was removed, and the reaction system was stirred at room temperature overnight. To the reaction mixture was added 10 ml of acetone, followed by stirring well, and followed by separation into solid and filtrate by filtration. To the solid was added another 10 ml portion of acetone, followed by stirring well, and followed by separation into solid and a filtrate. The resulting solid was washed with acetone in the same manner as above. All the filtrates were collected and evaporated in an evaporator to remove the solvent thereby to give pale yellow crystals (crude yield: 110.3%, GC purity: 95.5%). The crude product was purified by column chromatography (stationary phase: silica gel, mobile phase: ethyl acetate/methanol=6/1 by volume, Rf=0.46) to give the desired phosphorus-containing compound [I-3] as white crystals (overall yield: 56.5%; GC purity: 97.4%, $^{31}$P-NMR: 15.27 ppm). The results of the identification analyses are shown in FIG. 7 ($^1$H-NMR), FIG. 8 ($^{31}$P-NMR), and FIG. 9 (GC-MS).

Example 4

Synthesis of Phosphorus-Containing Compound [I-9]

In a 30 ml two-necked flask equipped with a rotor, a reflux tube, and an inlet for introducing $N_2$ were put 0.03 g (0.3 mmol) of magnesium chloride, 2.00 g (10 mmol) of 4,4'-methylenediphenol, and 30.67 g (200 mmol) of phosphorus oxychloride. The reaction mixture was heated until reflux while introducing $N_2$, followed by stirring overnight at that temperature. The introduced $N_2$ was vented from the upper end of the reflux tube and bubbled through an aqueous sodium hydroxide solution to have the by-produced hydrogen chloride trapped. After the reaction, the excess phosphorus oxychloride was removed in an evaporator to leave yellow liquid (intermediate). The intermediate product was dissolved in 10 ml of dehydrated tetrahydrofuran to prepare a THF solution of the intermediate product. Then, a 100 ml three-necked flask equipped with a rotor, a reflux tube, and a rubber septum was thoroughly dried, purged with nitrogen, and charged with 18.08 g (42 mmol) of a methylamine tetrahydrofuran solution and 4.25 g (42 mmol) of triethylamine while cooling in a salt-ice-water bath. After stirring for 5 minutes, the THF solution of the intermediate product was added thereto dropwise using a syringe taking care not to let the reaction temperature exceed 20° C. After the addition, the stirring was continued for 1 hour. The salt-ice-water bath was removed, and the reaction mixture was stirred at room temperature overnight. After completion of the reaction, the solvent and the excess of the starting material were removed in an evaporator to give pale yellow solid. The crude product was purified by column chromatography (stationary phase: silica gel, mobile phase: ethyl acetate/methanol=5/1 by volume, Rf=0.29) to yield the desired phosphorus-containing compound [I-9] as white solid (overall yield: 35.2%). The results of the identification analyses are shown in FIG. 10 ($^1$H-NMR) and FIG. 11 ($^{31}$P-NMR).

Example 5

The phosphorus-containing compound [I-2] obtained in Example 2 and weighing 57.1 mg (0.25 mmol) and 51.6 mg (0.25 mmol) of Adeka Glycirol ED-509S were allowed to react with each other in the presence of 2.3 mg (7.5 mol %) of DMAP as a catalyst in a nitrogen stream at 140° C. for 2 hours in accordance with the following reaction scheme. The results of $^1$H-NMR and $^{31}$P-NMR analyses shown in FIGS. 12 and 13, respectively, revealed that S4 (see below) was obtained as a main product.

[Chem. 12]

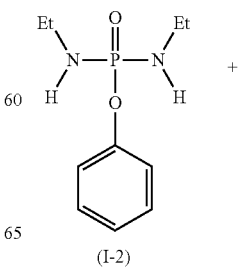

(I-2)

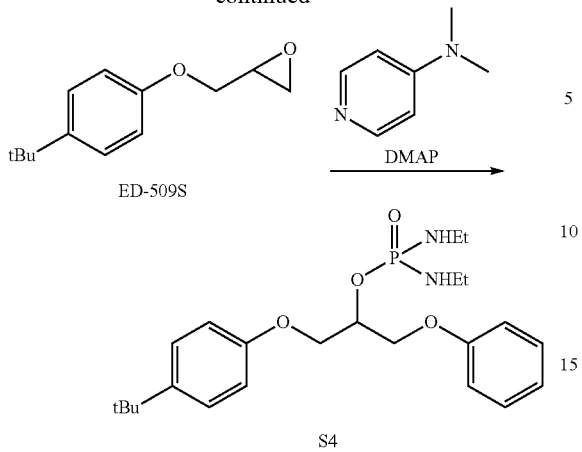

S4

Example 6

The phosphorus-containing compound [I-3] prepared in Example 3 and weighing 50.0 mg (0.25 mmol) and 51.6 mg (0.25 mmol) of Adeka Glycirol ED-509S were allowed to react with each other in the presence of 2.3 mg (7.5 mol %) of DMAP as a catalyst in a nitrogen stream at 130° C. for 2 hours in accordance with the following reaction scheme. The results of $^1$H-NMR and $^{31}$P-NMR analyses shown in FIGS. 15 and 16, respectively, revealed that S5 (see below) was obtained as a main product.

[Chem. 13]

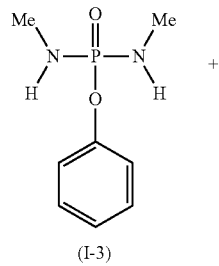

(I-3)

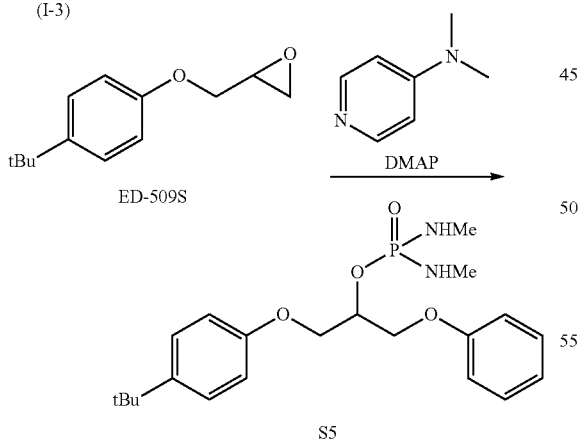

S5

Example 7

Adeka Resin EP-4100L weighing 1.02 g (100.0 phr), 0.16 g (15.7 phr) of the phosphorus-containing compound [I-9] of the invention, and 0.03 g (3.0 phr) of 2-ethyl-4-methylimidazole were mixed and heated in a thermostat at 150° C. for 3 hours and then at 180° C. for 3 hours to give a tack-free, brown cured product. The Tg of the cured product was found to be 140° C. as a result of DSC.

Examples of the invention proved that the phosphorus-containing compounds of the invention have reactivity with a glycidyl group. Compounding the phosphoric ester of the invention into an epoxy resin composition provides an epoxy resin cured product that is expected to have flame retardancy and a reduced dielectric constant without causing reduction in physical properties of the cured product.

The invention claimed is:

1. A phosphorus-containing compound represented by general formula (I):

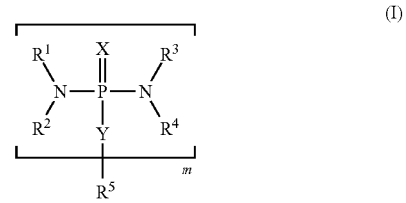

(I)

wherein m represents 1 or 2;
$R^1$, $R^2$, $R^3$, and $R^4$ each independently represent a hydrogen atom, or an alkyl group;
when m is 1, $R^5$ is represented by formula (1'),
when m is 2, $R^5$ is represented by one of formulae (2') or (3');
X represents an oxygen atom or a sulfur atom; and
Y represents an oxygen atom, or a sulfur atom;

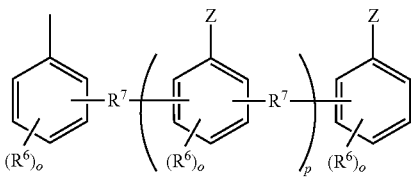

(1')

wherein $R^6$ represents a hydrogen atom or an alkyl group having 1 to 4 carbon atoms; O represents an integer of 1 to 3; p represents an integer of 0 to 50;
wherein Z is represented by formula (i')

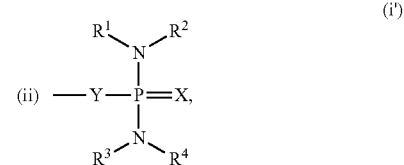

(i')

wherein $R^1$, $R^2$, $R^3$, $R^4$, X, and Y are as defined above;
$R^7$ is represented by formula (ii')

(ii')

wherein $R^8$ and $R^9$ each represent a hydrogen atom, $CH_3$, or $CF_3$;

(2')

-continued

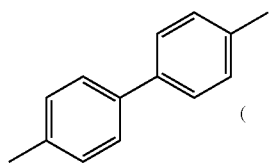
(3')

wherein n is 2.

2. The phosphorus-containing compound according to claim 1, wherein $R^1$, $R^2$, $R^3$, and $R^4$ each independently represent an alkyl group having 1 to 5 carbon atoms, and X and Y each represent an oxygen atom.

3. An epoxy resin curing agent comprising 5% to 100% by mass of the phosphorus-containing compound according to claim 1.

4. A curing epoxy resin composition comprising an epoxy resin and the epoxy resin curing agent according to claim 3.

5. An epoxy resin curing agent comprising 5% to 100% by mass of the phosphorus-containing compound according to claim 2.

6. The phosphorus-containing compound according to claim 1, selected from the group consisting of:

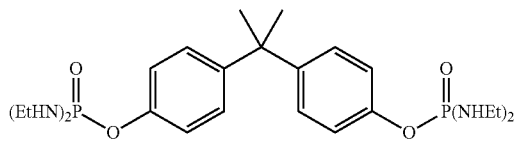

-continued

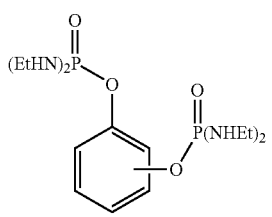

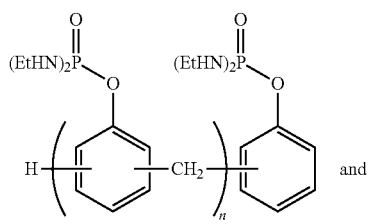

and

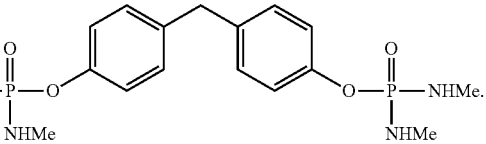

* * * * *